(12) United States Patent
Jacobson et al.

(10) Patent No.: US 7,727,363 B2
(45) Date of Patent: Jun. 1, 2010

(54) MICROFLUIDIC DEVICE AND METHODS FOR FOCUSING FLUID STREAMS USING ELECTROOSMOTICALLY INDUCED PRESSURES

(75) Inventors: Stephen C. Jacobson, Bloomington, IN (US); J. Michael Ramsey, Chapel Hill, NC (US)

(73) Assignee: UT-Battelle, LLC, Oak Ridge, TN (US)

( * ) Notice: Subject to any disclaimer, the term of this patent is extended or adjusted under 35 U.S.C. 154(b) by 1341 days.

(21) Appl. No.: 11/049,543

(22) Filed: Feb. 2, 2005

(65) Prior Publication Data

US 2006/0169588 A1    Aug. 3, 2006

(51) Int. Cl.
*F04B 19/04* (2006.01)
*F15C 1/04* (2006.01)
*F16K 31/02* (2006.01)

(52) U.S. Cl. .............. 204/229.5; 204/230.6; 204/643; 417/50; 417/211; 137/13; 137/826; 137/833; 251/129.05; 251/129.08; 251/339

(58) Field of Classification Search .......... 204/451, 204/601, 547, 229.5, 230.6, 643; 205/799
See application file for complete search history.

(56) References Cited

U.S. PATENT DOCUMENTS 5,858,187 A * 1/1999 Ramsey et al. .............. 204/452

6,183,206 B1 * 2/2001 Valenzuela et al. ............ 417/50
6,685,809 B1 * 2/2004 Jacobson et al. ............ 204/450
2002/0168278 A1 * 11/2002 Jeon et al. .................... 417/559
2003/0075446 A1 * 4/2003 Culbertson et al. .......... 204/451

OTHER PUBLICATIONS

Culbertson, C. T., et al. "Electroosmotically Induced Hydraulic Pumping on Microchips: Differential Ion Transport", Analytical Chemistry, vol. 72, No. 10, May 15, 2000, p. 2285-2291.*

* cited by examiner

*Primary Examiner*—Nam X Nguyen
*Assistant Examiner*—J. Christopher Ball
(74) *Attorney, Agent, or Firm*—Niels Haun; Dann Dorfman Herrell + Skillman, PC

(57) ABSTRACT

A microfabricated device employing a bridging membrane and methods for electrokinetic transport of a liquid phase biological or chemical material using the same are described. The bridging membrane is deployed in or adjacent to a microchannel and permits either electric current flow or the transport of gas species, while inhibiting the bulk flow of material. The use of bridging membranes in accordance with this invention is applicable to electrokinetically inducing fluid flow to confine a selected material in a region of a microchannel that is not influenced by an electric field. Other structures for inducing fluid flow in accordance with this invention include nanochannel bridging membranes and alternating current fluid pumping devices. Applications of the bridging membranes according to this invention include the separation of species from a sample material, valving of fluids in a microchannel network, mixing of different materials in a microchannel, and the pumping of fluids.

6 Claims, 30 Drawing Sheets intersection fill rinse

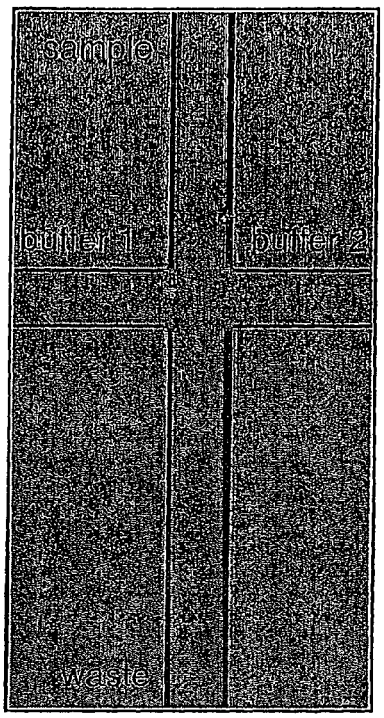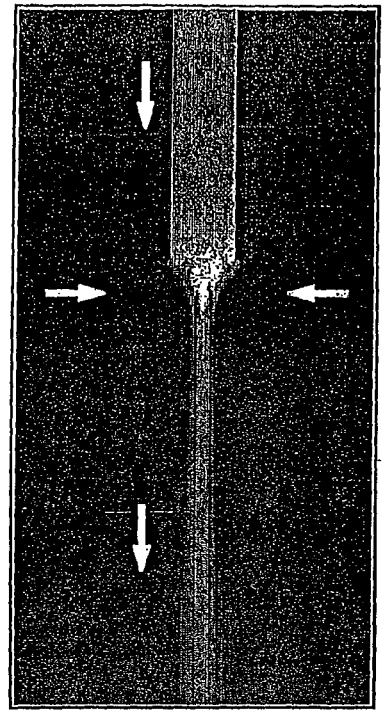
Fig. 24A
Fig. 24B
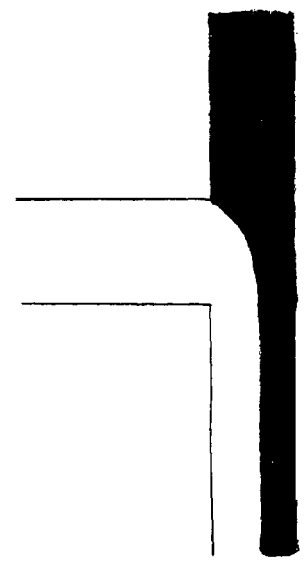
Fig 24C

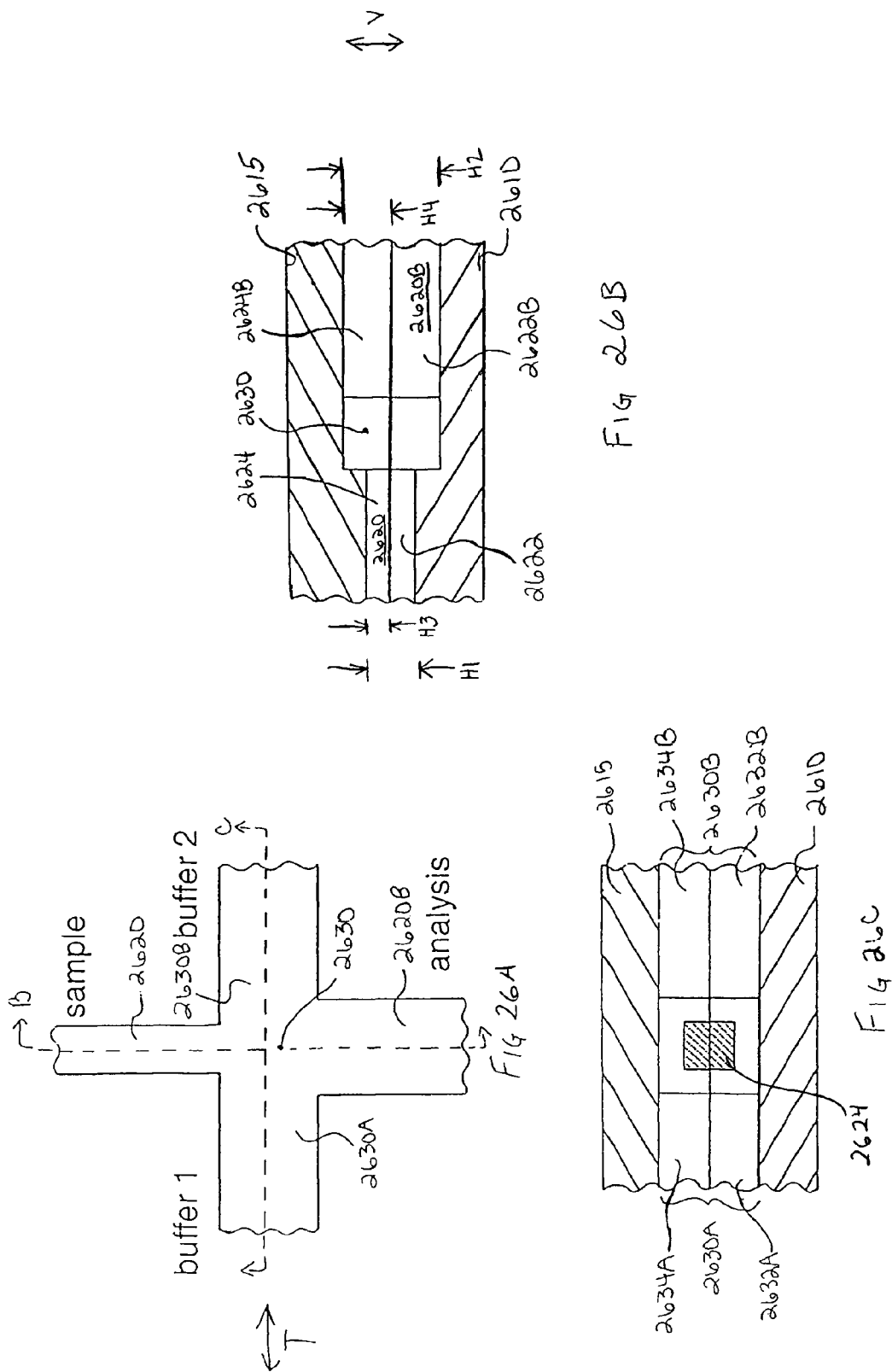

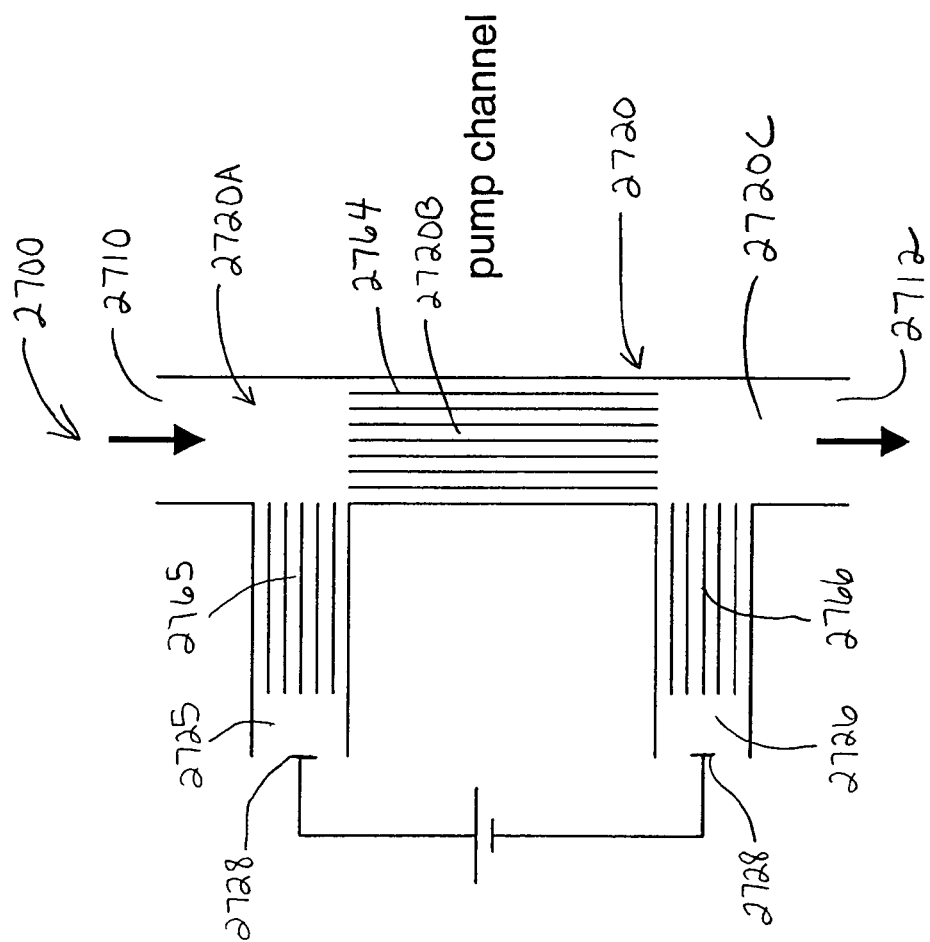

MICROFLUIDIC DEVICE AND METHODS FOR FOCUSING FLUID STREAMS USING ELECTROOSMOTICALLY INDUCED PRESSURES

The U.S. Government has a paid-up license in this invention and the right in limited circumstances to require the patent owner to license others on reasonable terms as provided for by the terms of contract DE-AC05-00OR22725 awarded by the U.S. Department of Energy.

FIELD OF THE INVENTION

This invention relates to microchip designs for the electrokinetic manipulation of fluidic chemical and biological materials. More specifically, this invention provides a microchip device which utilizes electrokinetic forces for the transport of materials through microchannels. A microchip device of this invention provides confinement of a fluidic stream in a region of a microchannel which is uninfluenced by an electric field.

BACKGROUND OF THE INVENTION

In order to facilitate the development of the biological and chemical sciences, microchip technologies are increasingly utilized to perform traditional chemical laboratory functions within a controlled microfabricated environment. These "on-chip" laboratories facilitate the precise transport and analysis of fluidic chemical and biological materials. Specifically, the decreased dimensions of the microchip devices provide integration of electronic and chemical processing technology while simultaneously yielding increased speed in analysis, reduction in reagent and/or sample consumption, and improved control in the automation of material manipulations.

Microfabricated devices that integrate chemical reactions with rapid analysis time have significant applications for high-throughput drug screening, automated analysis, and clinical chemistry. Microchips are characterized by reduced analysis time and reagent consumption, ease of automation, and valveless fluid control of sub-nanoliter volumes. A variety of electrically driven separations have been performed within microchannel networks. Microchips have also been developed for controlling chemical reactions, including arrays for solid-phase chemistry, reaction wells for polymerase chain reactions, channels with immobilized enzymes for flow injection analysis, and manifolds for homogenous enzyme assays. A microfluidic device using electrokinetic mixing of the organic solvents and reagents for the formation of an azo dye has been demonstrated.

The ability to design and machine channel manifolds with low-volume connections renders microchips suitable for combining several steps of an analytical process on one device. Microchips that combine chemical reactions with the speed and scale of CE analysis have been demonstrated for pre- and post-separation reactions, for DNA restriction digests with fragment sizing, and for cell lysis, multiplex PCR amplification and electrophoretic sizing.

Presently, chemical and biological materials are transported on microchips by way of electrokinetic techniques or an external pumping apparatus. The use of an external pumping apparatus is disfavored, however, because it demands additional hardware that is bulky and difficult to interface with the microchips. On the other hand, electrokinetic techniques, i.e., electroosmotically induced fluid flow or electrophoretic migration of ions, are the preferred methods of manipulating biological and chemical materials on microchip devices.

Electroosmosis is the bulk flow of fluid due to the combined effects of an electrical double layer in the presence of an axial electrical field. See, e.g., C. L. Rice and R. Whitehead, "Electrokinetic Flow in a Narrow Cylindrical Capillary", J. of Phys. Chem. (1965). The high density of ions in the diffuse region of the double layer are pulled electrostatically by the electric field along the walls of the channel. The layer of ions acts like a sleeve that is being pulled along the wall which adds momentum to the fluid by viscous drag. Under steady state conditions, which are reached in a microsecond timescale for the dimensions discussed herein, all fluid which is farther from the wall than the diffuse region are traveling at the same velocity. For example, water at pH 8 in a glass microchannel would travel at a velocity of $\approx 1$ cm/s with an electric field strength of $\approx 1$ kV/cm. Electrophoresis is the velocity imparted to an ion in solution when exposed to an electric field. The velocity of the ion is determined by the charge of the ion, the electric field strength, the viscosity of the solvent and the hydrodynamic radius of the ion. The direction of the ion movement depends on the direction of the electric field vector and the polarity of the charge on the ion. Electrophoresis necessarily only transports charged species. Electroosmosis imparts a velocity to all ions and neutral species. Under conditions where both electroosmosis and electrophoresis are operative, the net velocity of an ion will be the vector sum of the electroosmotic and electrophoretic velocities.

Electrokinetic transport mechanisms have been highly effective for demonstrating a number of highly useful experiments as identified above. A deficiency of presently demonstrated devices is the inability to make electrical contacts directly within microchannels. Efforts have been made to make such electrical contacts using a metal film that is photolithographically deposited onto a glass substrate so as to make contact with the fluidic microchannels. Such electrodes produce electrolysis products, most notably, oxygen and hydrogen gas from water, in all cases except under very limited conditions. The formation of a gas bubble can quickly separate the fluid in a microchannel and produces a nonconducting region which hinders the electrokinetic transport mechanisms.

SUMMARY OF THE INVENTION

The present invention provides a microfabricated device for liquid phase chemical and biological analysis. The device includes a substrate microfabricated with a series of channels and reservoirs. In accordance with this invention at least two of the microfabricated channels either intersect or are in close proximity to each other but do not overlap. A bridging membrane is created in one of the intersecting channels or between the two adjacent channels. The bridging membrane permits an ionic electric current flow or gas transport while inhibiting bulk fluid flow therethrough. Reservoirs are formed in fluidic communication with the etched channels and are electrically connected with a high voltage power source to provide an electrical potential for electrokinetically driving and/or injecting materials from the reservoirs into the channels.

In accordance with one aspect of the present invention, a microfabricated device for spatially confining a sample fluid stream in an electric field free region of the microfabricated device is provided. The microfabricated device includes a focusing chamber formed in a surface of a substrate. A sample channel is provided in the surface of the substrate for conducting a sample fluid stream therethrough. The sample channel includes a first end in fluid communication with a source of a sample fluid and includes a second end in fluid communication with the focusing chamber. A focusing channel is also provided in the surface of the substrate for conducting a first focusing fluid stream therethrough. The focusing channel includes a first end in fluid communication with a source of focusing fluid and a second end in fluid communication with the focusing chamber. The microfabricated device further includes means for driving the respective streams of the sample and focusing fluids through the respective channels into the focusing chamber so that the focusing fluid stream spatially confines the sample fluid stream in an electric field free region within the focusing chamber.

An object of the present invention is to provide a microfabricated device for performing sample loading and injection procedures that minimize electrochemically generated products in the transported sample.

Another object of the present invention is to provide reagent processing of electrokinetically driven products in a microfabricated device having a region that is uninfluenced by an electric field.

A further object of the present invention is to provide a microfabricated device which enables the transport of fluidic chemical and biological materials by electroosmotic forces into a region uninfluenced by an electric field.

Another object of the present invention is to provide a microfabricated device capable of concentrating ionic species.

A further object of the present invention is to provide a microfabricated device for separating or purifying a sample material.

Another object of the present invention is to provide a microfabricated device to facilitate the removal of electrochemically generated gas species.

A still further object of the present invention is to provide a microfabricated device to generate positive or negative pressure to facilitate hydraulic transport of gases or liquids.

Another object of the present invention is to provide a microfabricated device to effect valving in microfluidic structures.

A further object of the present invention is to provide a microfabricated device to effect transport of liquids or gases along a selected direction through the use of one or more check valves.

BRIEF DESCRIPTION OF THE DRAWINGS

The foregoing summary, and the following detailed description, will be better understood when read in conjunction with the attached drawings, in which:

FIG. 5A is an enlarged view of the intersection of the side channel and analysis channels of FIG. 5 showing the location of the bridging membrane;

FIG. 24A is a white light image of the cross intersection on a microchip in accordance with FIG. 19A;

FIG. 24B shows a fluorescence image of the cross intersection of FIG. 24A showing a sample stream focused by buffer streams;

FIG. 24C is a schematic diagram of a T-intersection showing a sample stream focused by a single buffer stream;

FIGS. 26A-C are schematic diagrams of arrangements of microchannels in accordance with yet another aspect of this invention for accomplishing two dimensional focusing of a stream of fluidic material; and FIG. 27 is a schematic diagram of an arrangement of microchannels and bridging membranes comprising nanochannels for transporting a material along a microchannel.

DETAILED DESCRIPTION OF THE PREFERRED EMBODIMENTS

Figure 1:
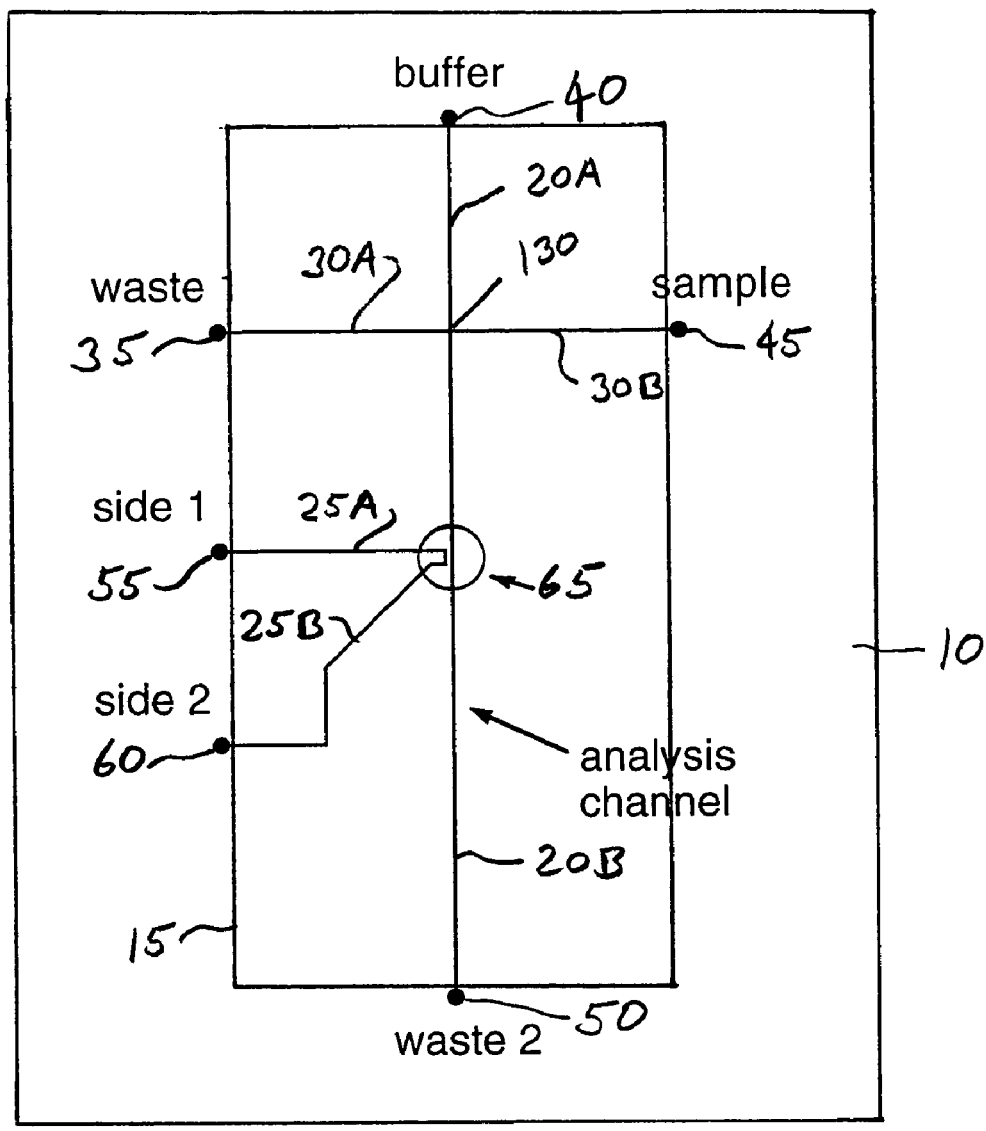
FIG. 1 is a schematic diagram of a fluidic microchip having a bridging membrane in accordance with the present invention.

A microfabricated device in accordance with the present invention is described in connection with several embodiments of microchannel networks utilizing a bridging membrane that is operable to pass ionic current, but minimize bulk fluid flow or transport of larger molecules, e.g. DNA. The bridging membrane allows electrical connection to fluidic microchannels without the problems related to electrolysis. This capability enables a number of important fluidic manipulations to be realized on microfabricated structures designed for the analysis and synthesis of chemical and biochemical materials.

A device in accordance with the present invention is particularly useful in connection with the analysis or processing of materials which are affected by electrophoretic bias. For example, post electrophoretic separation derivatization of a sample with a reagent would benefit from the devices of the subject invention. Also, the microfabricated device of the present invention permits electrochemical detection schemes in which a detection cell needs to be isolated from the electric field that facilitates transport of the sample material.

A device according to this invention uses the electroosmotic phenomenon to drive fluids, but includes a bridging membrane to isolate electric fields generated in the channels of the microfabricated device. The bridging membrane permits ionic current or gas to pass but minimizes or restricts bulk fluid flow. In a first embodiment, the bridging membrane provides a connection between a first channel and a second channel carrying materials to be analyzed or processed. One application of this configuration involves using the bridging membrane in a fluidic microchip for facilitating DNA concentration enhancement.

A second embodiment includes a first channel which is filled with a polyacrylamide gel as the bridging membrane. The gel is disposed in the first channel adjacent to the second or analysis channel of the microfabricated device.

A third embodiment utilizes the bridging membrane to facilitate sample loading and injection procedures such that electrochemically generated byproducts in the sample are minimized. A second application of a device according to this invention uses a bridging membrane for separating or purifying a sample material.

A fourth embodiment includes a channel with a thin film electrode and a bridging membrane which facilitate the removal of electrochemically generated gas species from the microfabricated channel.

A fifth embodiment includes a channel with one or more check valves which may be used as to transport fluid in a channel of a microfabricated device.

Additional applications employ bridging membranes to pump liquids or gases through microchannels. A further application employs such pumping to confine a stream of sample fluid in at least a first direction and to draw such a confined stream into an analysis portion of the microchip which portion is uninfluenced by an electric field. Still further applications employ bridging membranes to effect valving in microfluidic structures. Yet further applications of this invention utilize bridging membranes for generating elevated pressures in a microchannel or to effect mixing of materials in a microchannel.

Adjacent Channel Embodiment

Figure 1A:
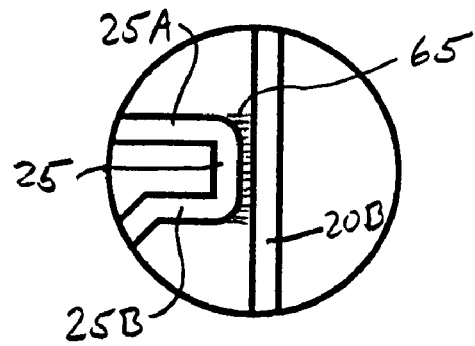
FIG. 1A is an enlarged view of the bridging membrane shown in FIG. 1.
Figure 1B:
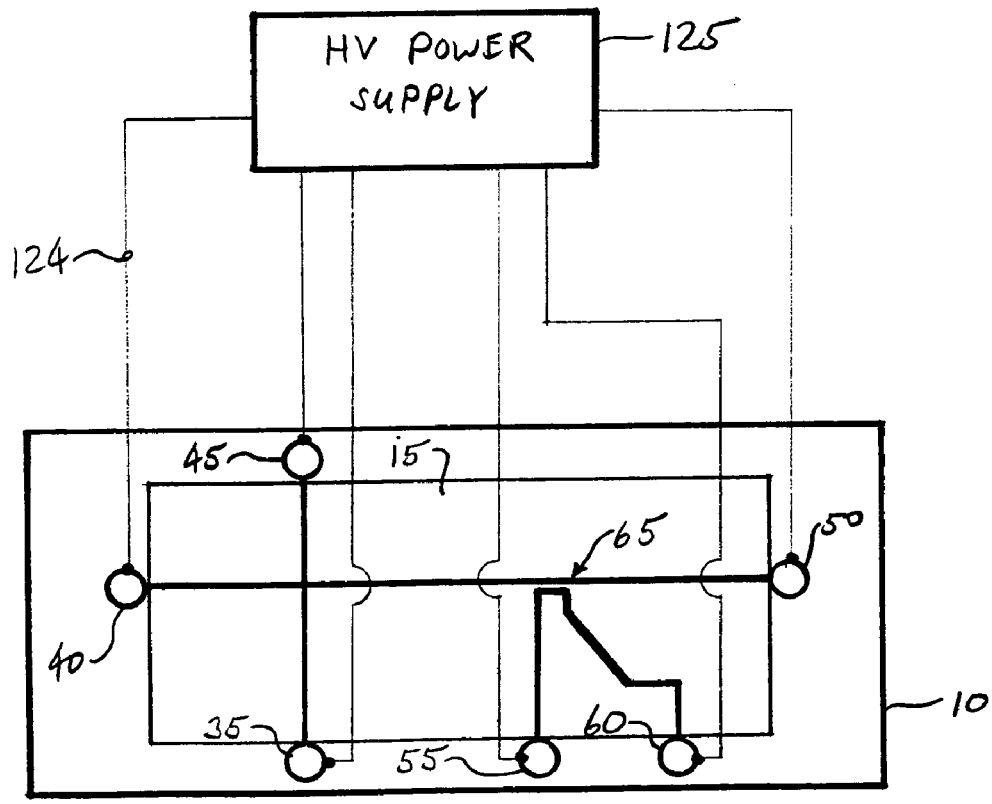
FIG. 1B is a schematic diagram showing the electrical connections to the microchip of FIG. 1.

Referring now to FIGS. 1, 1A, and 1B there is shown a microfabricated device labeled 5A in accordance with the present invention. Device 5A is fabricated from a solid substrate material 10. Glass is a preferred substrate material because it etches isotropically. However, silicon may be used instead because of the well developed technology permitting its precise and efficient fabrication. Also, other materials such as polymers, quartz, fused silica, sapphire, or plastics may be used. A series of microchannels 20A, 20B, 25, 25A, 25B, 30A, and 30B are formed in the top surface of the substrate 10 for facilitating the electroosmotic transport of biological and chemical materials. The microchannels 20A, 20B, 30A, and 30B intersect at a channel junction 130. Microchannel 25 interconnects side channels 25A and 25B adjacent to analysis microchannel 20B. A cover plate 15 appropriately affixed over the top surface of the substrate 10 seals the microfabricated surface of device 5A.

The microchip device 5A is fabricated using micromachining methods known to those skilled in the art. The micromachining methods available include film deposition processes such as spin coating and chemical vapor deposition, laser fabrication or photolithographic techniques such as UV or X-ray processes, or etching methods which may be performed by either wet chemical processes or plasma processes. Preferably, the microchannels 20A, 20B, 25, 25A, 25B, 30A, and 30B are formed on substrate 10 using a positive photoresist, photomask, and UV exposure. The channels are etched into the substrate 10 in a dilute, stirred HF/NH4F bath.

Cover plate 15 is bonded to the substrate 10 over the etched microchannels 20A, 20B, 25, 25A, 25B, 30A, and 30B by hydrolyzing the surfaces, spin-coating sodium silicate or potassium silicate onto the cover plate 15, bringing the substrate and cover plate into contact with each other, and then processing the assembly at temperatures typically ranging from about room temperature up to about 500° C. A suitable procedure is described in our copending application Ser. No. 08/645,497, the specification of which is incorporated herein by reference.

Microchip device 5A, includes a first waste reservoir 35, a buffer reservoir 40, a sample reservoir 45, a second waste reservoir 50, and first and second side reservoirs 55 and 60. The reservoirs are bonded to the substrate 10 over the terminal ends of micro-channels 30A, 20A, 30B, 20B, 25A, and 25B, respectively. The reservoirs of microchip device 5A are storage cells for liquid phase biological and chemical materials. The reservoirs supply materials for fluidic transport through the microfabricated channels.

As shown in FIG. 1B, a high voltage power supply 125 is connected to the reservoirs of device 5A to provide electric potentials thereto. A plurality of platinum wire electrodes 124 electrically connect the power supply 125 to the reservoirs of the microchip device 5A and contact the materials contained therein. The high voltage power supply 125 may be formed from a plurality of independent voltage sources or as a single voltage source and voltage divider network with a plurality of output terminals each providing a different voltage levels. The electrokinetic driving forces are created by providing a potential difference between the various reservoirs in a controlled manner. Applied potentials on electrokinetically driven microchips are typically 1-3 kV, but can be higher or lower and the desired polarity depends on the experimental conditions.

Figure 2:
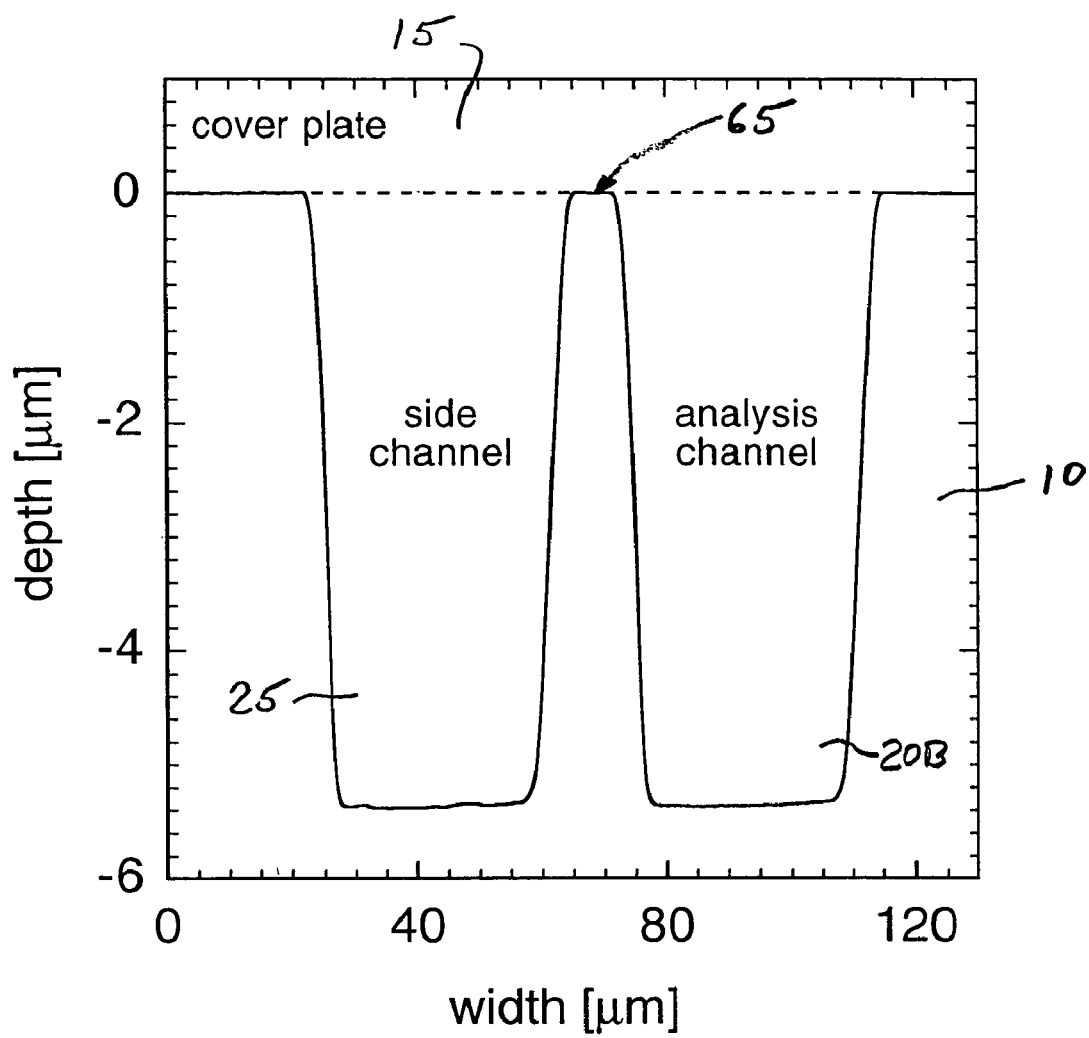
FIG. 2 is a graph showing a cross-sectional profile of two channels and a bridging membrane used in the microchip of FIG. 1.

Microchip device 5A as seen in FIG. 1A has a bridging membrane 65 (i.e., a thin electrically conductive porous glass layer) between microchannel 20B and channel 25. The microchip 5A has two channels in close proximity to each other. The distance between adjacent channels will vary depending on the etch time used to form the channels in the substrate, 0-35 μm bridges are typical. In the case of glass for example, the etch is isotropic so the longer the etch the closer the two channels come to physically connecting. Also, a low temperature bonding technique is used in order to generate a thin porous layer between the cover plate 15 and the substrate 10 at the bridging membrane junction 65. For microchip 5A, the preferred channel separation distance between channel 20B and channel 25 is about 6 μm. FIG. 2 shows a cross-sectional profile of an embodiment of channels 20B and 25, cover plate 15, and bridging membrane 65. The depth and width of the channels were determined with a stylus profilometer.

There are several potential alternative methods for forming a bridging membrane between two adjacent channels such as described for device 5A. The adjacent channels can be formed in sufficiently close proximity and the cover plate fixed to the substrate using a conventional high temperature bonding procedure. An electrical potential of sufficient strength can then be applied to the channels on opposite sides of the bridging membrane to thereby form electrical breakdown channels. Such breakdown channels provide a path for electrical conduction but have dimensions near that of the electrical double layer responsible for electroosmotic flow. Such channels are less efficient in producing electroosmotic flow and thus can act as bridging membranes. Another method of forming a bridging membrane is to directly fabricate the bridging channel(s) to have dimensions similar to the electrical double layer and thus allow electrical conduction without significant fluid conduction.

Working Examples

Figure 3A:
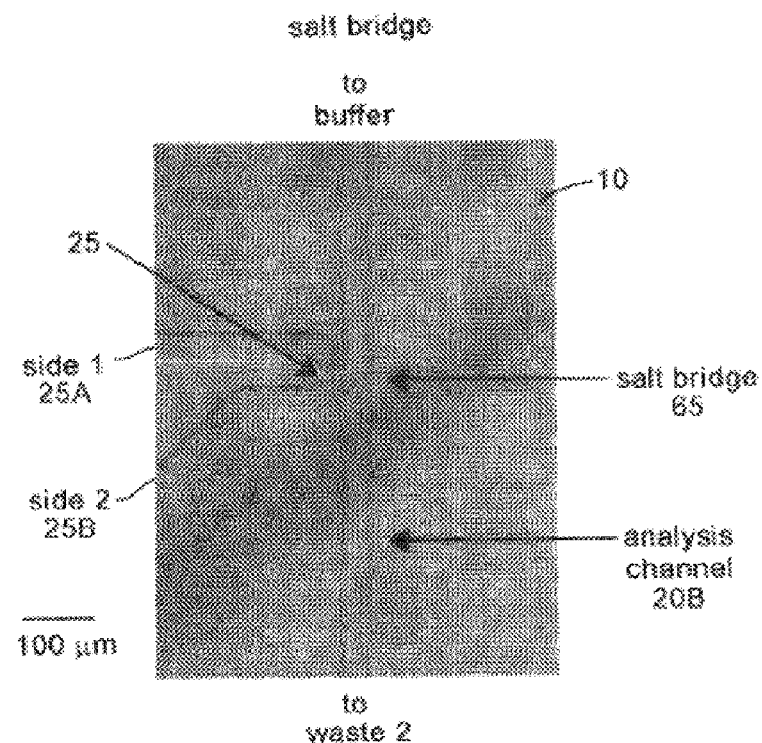
FIG. 3A is a white light image of the bridging membrane of FIG. 1 in accordance with the present invention.
Figure 3B:
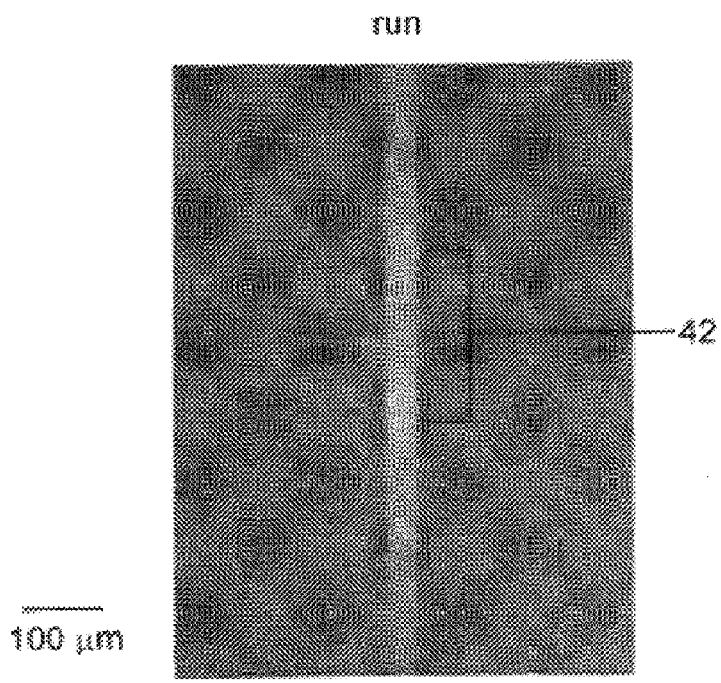
FIG. 3B is a fluorescence image of the rhodamine B buffer pumped beyond the bridging membrane connection of the microchip in FIG. 1.

Referring now to FIG. 3A, there is shown a portion of a physical embodiment of a microchannel device such as device 5A. The device shown utilizes a porous glass layer as the bridging membrane. The analysis channel 20B and the side channels 25A and 25B have been formed on the substrate 10. Operation of device 5A will now be described with reference to FIGS. 1 and 3B. A plug 42 of rhodamine B in a sodium tetraborate buffer is first loaded into analysis channel 20B using a fixed volume valve arrangement in which electric potentials of 0.6, 0.8, 0, and 0.6 kV are applied to the buffer reservoir 40, the sample reservoir 45, the first waste reservoir 35, and the first side reservoir 55, respectively. (0 kV corresponds to ground potential). Electric potentials of 1.0, 0.7, 0.7, and 0 kV are then applied to the buffer reservoir 40, sample reservoir 45, first waste reservoir 35, and first and second side reservoirs 55 and 60, respectively, to provide the electrokinetic driving force for transporting the plug 42 of rhodamine B in the analysis channel 20B. No voltage was applied to second waste reservoir 50, thereby allowing its potential to float. The plug of rhodamine B is transported in the analysis channel 20B by electroosmotic flow between the junction 130 and bridging membrane 65, and by electroosmotic pressure induced in the analysis channel 20B beyond the bridging membrane 65. A small fraction of the rhodamine B from plug 42 moves across the bridging membrane 65 to channel 25, but the bulk of the fluid material flows past the bridging membrane 65 as shown in FIG. 3B.

Figure 4:
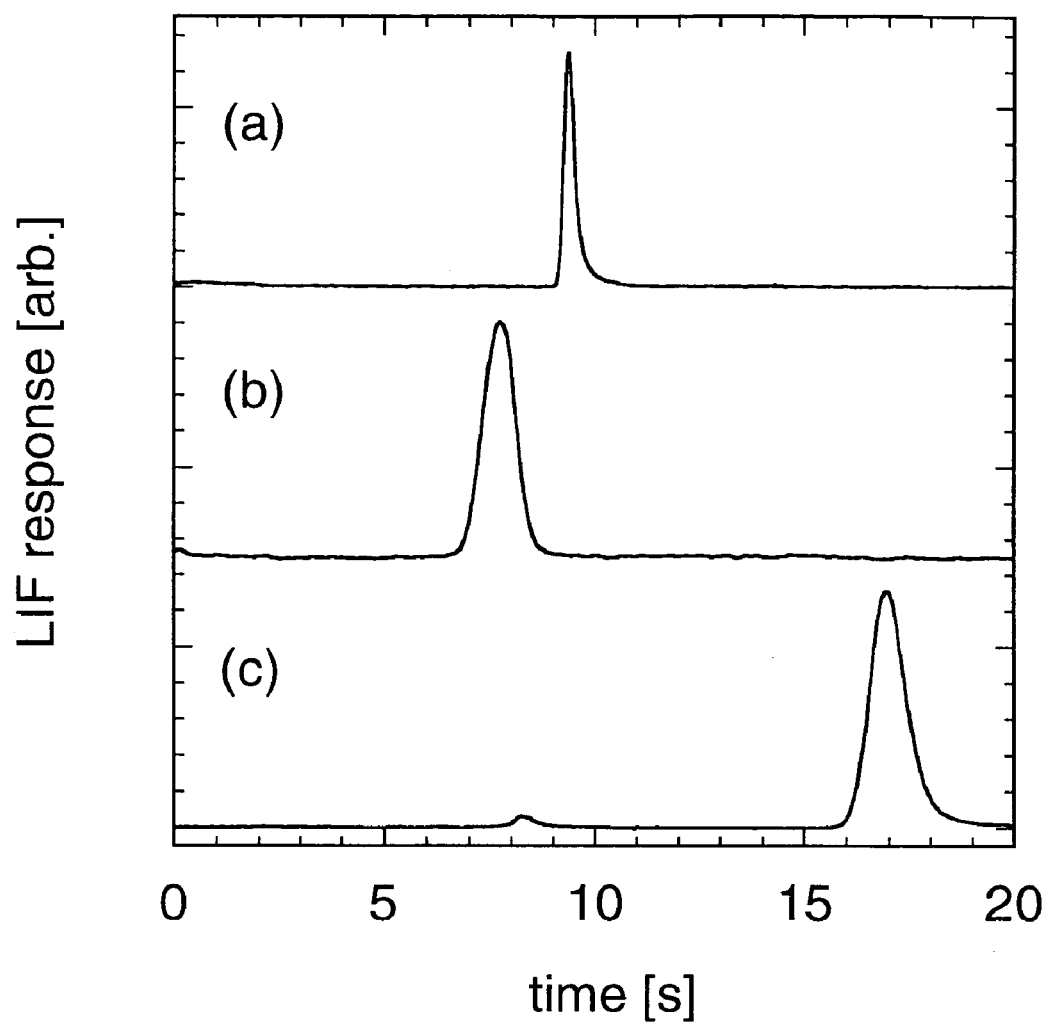
FIG. 4 is a graph of three profiles of a rhodamine B marker used to measure (a) electroosmotic flow without a bridging membrane, (b) electroosmotic flow using a bridging membrane, and (c) flow 10 mm beyond the junction using the bridging membrane.

The velocity of the sample plug 42 was measured using a single point detection scheme. Microchip 5A was first tested for electroosmotic flow under standard operating conditions, i.e., with no electric potential applied to the bridging membrane 65. The buffer reservoir 40, the sample reservoir 45, the first waste reservoir 35, and the second waste reservoir 50 were energized at voltages of 1.0, 0.7, 0.7, and 0 kV, respectively, to transport the sample plug along the analysis channel. No electric potential was applied to the other reservoirs. The measured electroosmotic velocity of the plug 42 in the vicinity of the bridging membrane was 1.07 mm/s. The rhodamine B concentration profile was monitored in the analysis channel 20B at a point adjacent to the bridging membrane 65. Graph (a) of FIG. 4 shows the timing of the sample as it passes the bridging membrane 65.

To measure the velocity with the side channels 25, 25A, and 25B engaged, i.e., with the bridging membrane in operation, electric potentials of 1.0, 0.7, 0.7, and 0 kV were applied to the buffer reservoir 40, sample reservoir 45, first waste reservoir 35, and first side reservoir 55, respectively. No electric potential was applied to the second waste reservoir 50 or the second side reservoir 60. The electroosmotic velocity measured in the vicinity of the bridging membrane was 1.29 mm/s. The profile was again monitored at the bridging membrane junction 65. Graph (b) of FIG. 4 shows the timing of the sample as it passes the bridging membrane 65. Graph (c) shows the timing of the same sample as obtained 10 mm downstream from the bridging membrane in a region of the analysis channel 20B that is free of an electric field. The velocity of the rhodamine B in the analysis channel 10 mm beyond the junction was measured as 1.09 mm/s. The velocity difference corresponds to an estimated pressure generated in the analysis channel of about 0.10 bar from the use of the bridging membrane.

The pressures or vacuums that are generated using these concepts depend on the dimensions of the channels, the interfacial characteristics and the properties of the fluid. The equation below shows the pressure dependence on some of these parameters.

$$P = \frac{3\varepsilon_0 \varepsilon \zeta E L}{\pi d^2}$$

The parameter $\varepsilon_0$ is the permittivity of free space, $\varepsilon$ is the fluid dielectric constant, $\zeta$ is the zeta potential, E is the axial electric field strength, L is the channel length over which electrokinetic pumping is taking place, and d is the channel depth. Greater pressures can be generated by reducing the channel depth, but not without bounds. When the channel depth approaches the electrical double layer thickness, electroosmotic pumping becomes less efficient with corresponding reductions in the average fluid velocity produced for a given electrical field, as understood by those skilled in the art. The variation of fluid flow and effective pressure generation with varying channel depths and double layer thicknesses, at fixed electrical field strength or current, provides the ability to design structures that generate for different purposes as described in this application. Effective pressures that can be electrokinetically generated can be controlled with channel depth and length. In addition by making channel dimensions similar to the double layer thickness, fluid conduction can be inhibited while maintaining electrical current.

Figures 10A, 10B:
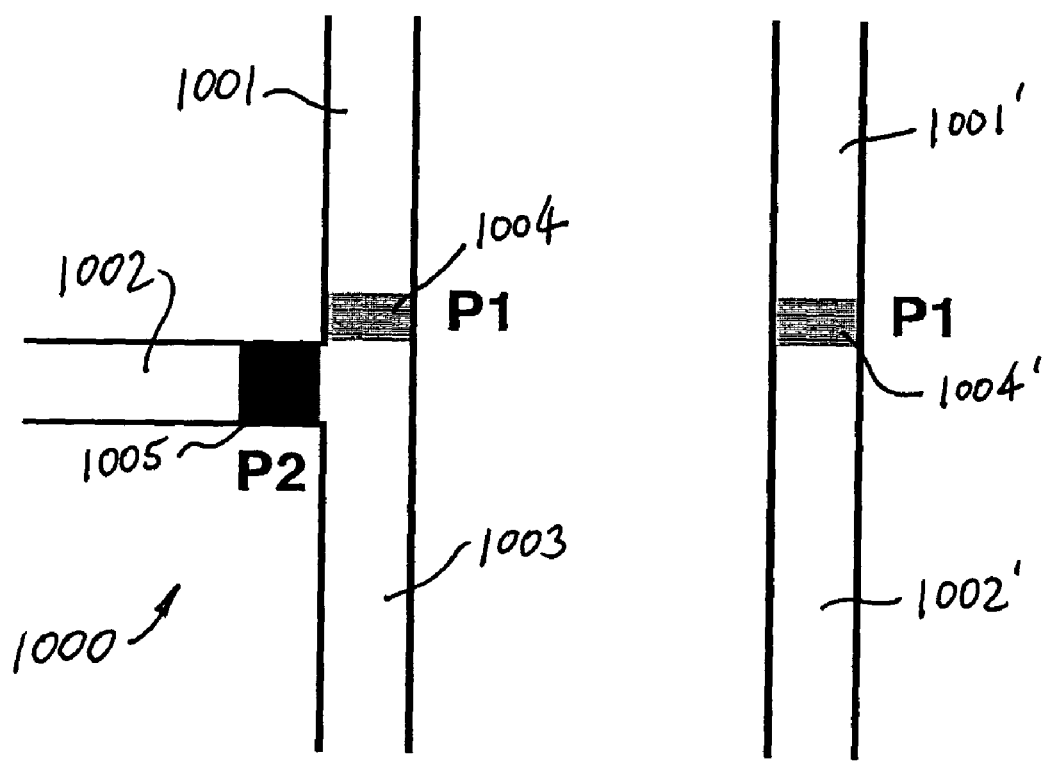
FIG. 10A is a schematic diagram of a "tee" microchannel network having a bridging membrane in two of the microchannels thereof.
FIG. 10B is a schematic diagram of a single, straight channel of a microchannel network having a bridging membrane disposed therein.

One way to effectively reduce the channel depth or pumping depth dimension is to form a porous network of channels such as formed by the silicate bonding methods used in the working examples described hereinabove. The pore size of the bridging membrane acts as the channel depth in the equation above for the pressure P, while the many separate paths through the membrane increase the flow rate of fluid. An example of such a device is shown in FIG. 10A. A tee microchannel network 1000 is formed with channel segments 1001, 1002, and 1003. A bridging membrane 1004 is formed in channel 1001 and a second bridging membrane 1005 is formed in channel 1002. The bridging membranes 1004 and 1005 are positioned near the intersection of the channels.

To generate pressure in channel 1003 a voltage is applied between the entrance to channel 1001 and the entrance to channel 1002 so as to transport fluid from channel 1001 to channel 1002. The pumping characteristics, i.e., the fluid flow rate at a given electric field strength, are different for the two membranes. Membrane 1004 is formed to provide a higher pumping rate than membrane 1005. Under such conditions and given zero flow rate out channel 1003, a pressure will be generated in channel 1003 corresponding to the pressure drop across membrane 1004. Such generated pressures could be used to push a mobile phase through channel 1003 that is packed with stationary support particles while providing an electric field free region in channel 1003. Adjusting the applied potential to reverse the direction of fluid transport will allow a vacuum to be created in channel 1003.

An alternative form of this arrangement is shown in FIG. 10B which includes an upper channel 1001' and a lower channel 1002'. The upper channel 1001' has a bridging membrane 1004' formed therein. When a voltage is applied between the entrances to channels 1001' and 1002' so as to move fluid from channel 1001' to channel 1002', a pressure is generated in the lower channel 1002' corresponding to the pressure drop characteristics of bridging membrane 1004'. However, this implementation results in an electric field being present in the lower channel 1002', the high pressure microchannel segment.

Figure 8:
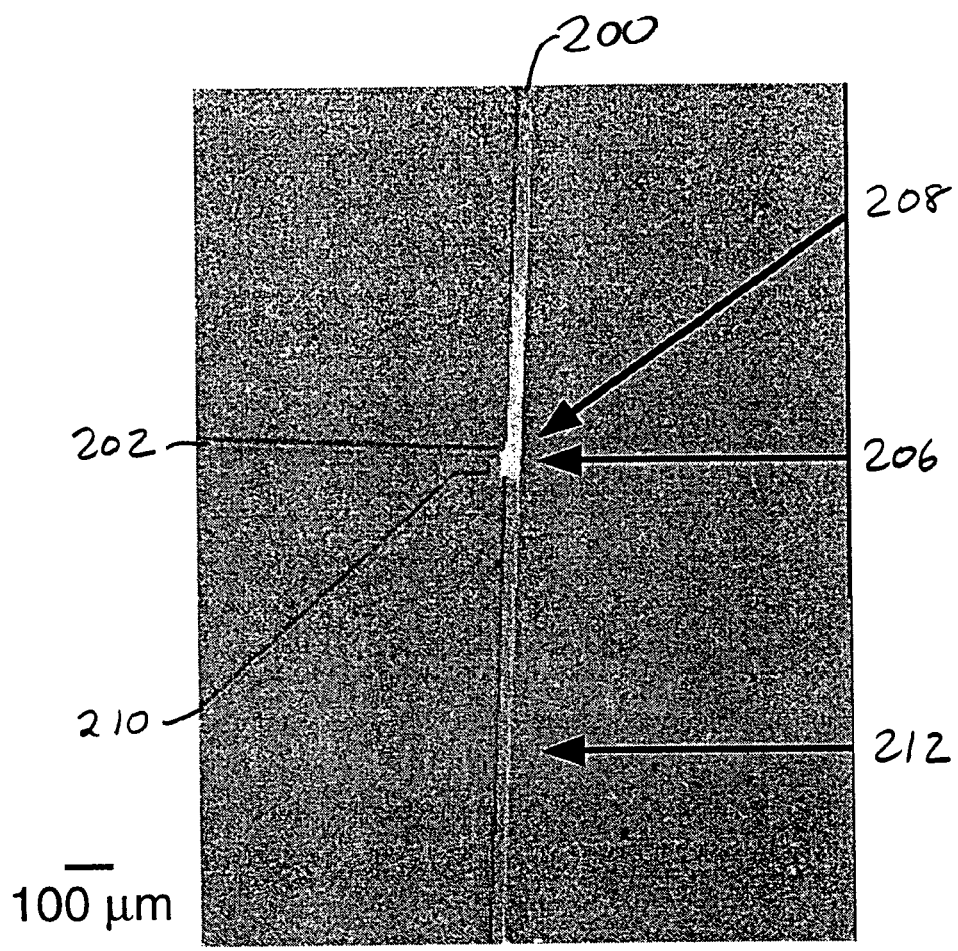
FIG. 8 is a backlit image of a further embodiment of a bridging membrane according to this invention.

Referring now to FIG. 8, there is shown a second working example embodied as microchip 5B in accordance with the present invention. The working example illustrates the use of microchip 5B for concentration enhancement of DNA using a bridging membrane incorporated into the microfluidic network formed on the chip. The microfabricated bridging membrane structure of microchip 5B is similar in design to microchip 5A shown in FIG. 1 and described previously herein. FIG. 8 is a backlit image of an actual microchip combined with a fluorescence image of the DNA material 208 concentrated in the analysis channel 212 at the bridging membrane 206 (bright spot at the bridging membrane). The concentration enhancement occurs when an electrical potential is applied between the sample channel 200 and the first side channel 202. No electrical potential is applied to the analysis channel 212 in this case, but an electric potential of the same polarity as applied to the sample channel 200, if applied to waste channel 212, would further assist in confining the spatial extent of the concentrated DNA sample 208 adjacent to the bridging membrane 206. The bridging membrane 206 allows small ions to pass but prevents the larger molecules of the DNA 208 from migrating through the bridging membrane 206 in the presence the electric field. The bridging membrane thus acts as a physical barrier through which the DNA molecules 208 cannot pass and, over time, the DNA 208 accumulates at the bridging membrane junction 206. The amount of DNA 208 collected at the bridging membrane 206 is related to the electric field strength, the time of accumulation, and the electrophoretic mobility of the DNA 208. In this example, the sample channel 200 is grounded, and 1 kV is applied to the second side channel 210. The accumulation time is approximately 1 minute. The analysis and side channels, 212 and 202 respectively, are coated with covalently linked linear polyacrylamide to minimize electroosmotic flow and are filled with 3% linear polyacrylamide, a common sieving medium for DNA separations.

Figure 9:
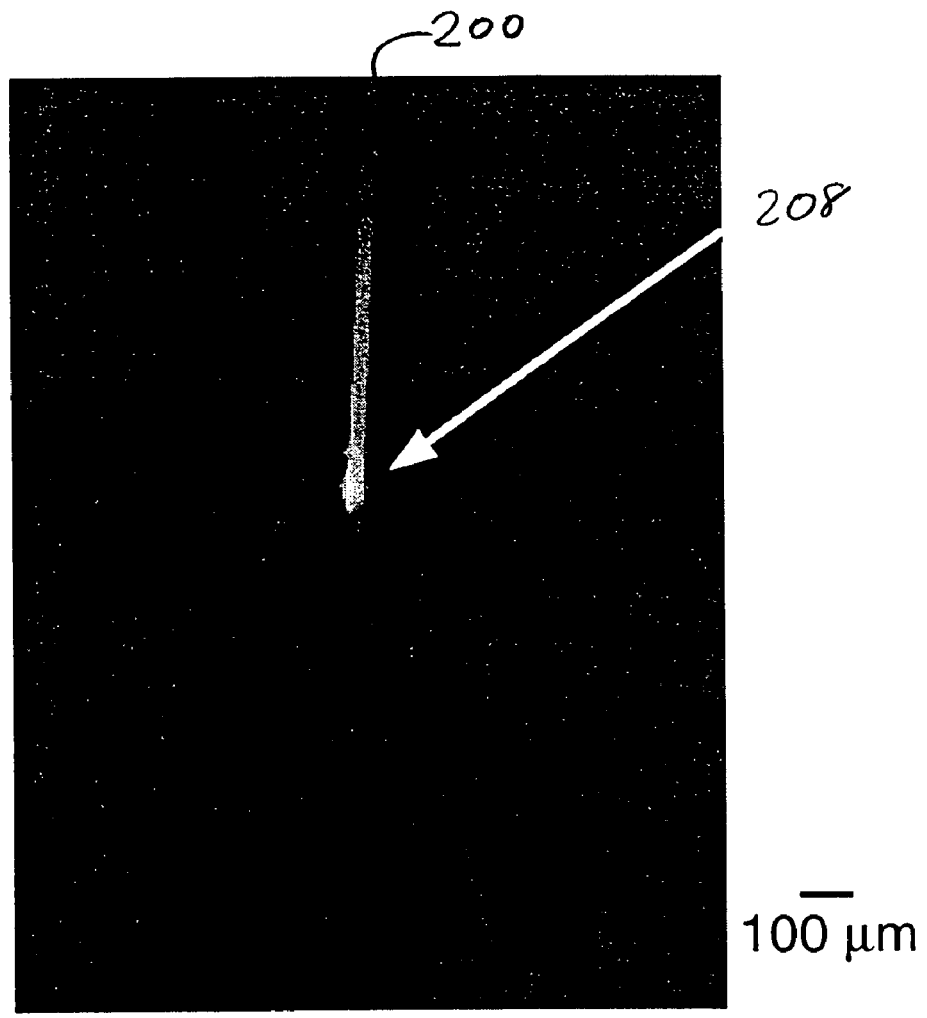
FIG. 9 is a fluorescence image of DNA concentration at the bridging membrane of FIG. 8.

FIG. 9 shows a fluorescence image of the double stranded DNA 208 (ΦX-174, He III digest) intercalated with a dye, TOPRO, and excited using an argon ion laser (514.5 nm) without backlighting of the bridging membrane connection 206. The bright spot at the center of the image is the DNA material 208 that has been transported from the sample reservoir 200 and concentrated at the bridging membrane 206. This technique can be used to concentrate either single or double stranded DNA. Clearly the intensity of the fluorescence is greater in the vicinity of the bridging membrane 206 than on the sample reservoir side of the analysis channel or in the analysis channel below the bridging membrane 206. Also, with the addition of a channel to the microchip design both a constant volume or variable volume valve can be implemented to inject a sample onto the analysis channel 212 following concentration enhancement at the bridging membrane. Such a DNA concentration enhancement tool would be valuable for DNA analysis when DNA concentrations would otherwise be too low to measure using standard techniques. It will be readily apparent to those skilled in the art that such as device is useful for other types of materials that are to be analyzed such as proteins and synthetic polymers.

Intersecting Channel Embodiments

Figure 5:
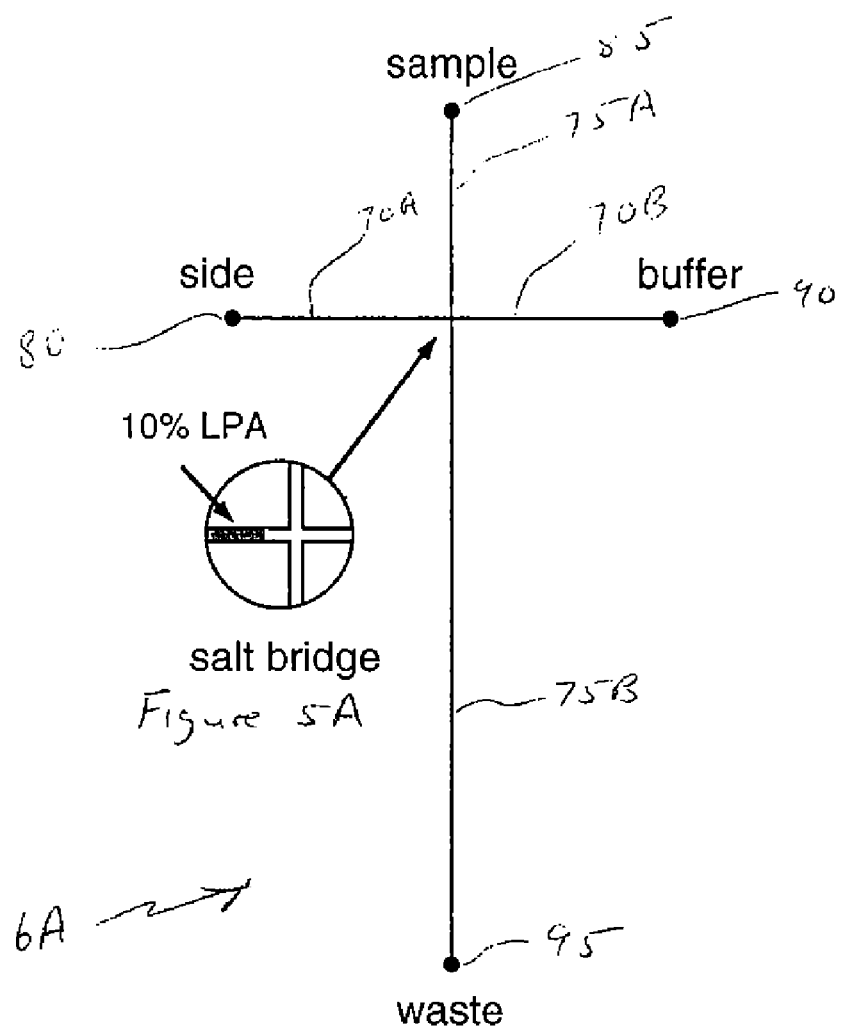
FIG. 5 is a schematic diagram of a second embodiment of a microchip in accordance with the present invention.

Referring now to FIG. 5, there is shown another embodiment of a microchip 6A in accordance with the present invention. Microchip 6A has side channel portions 70A and 70B and analysis channel portions 75A and 75B formed thereon. The side channel portions 70A, 70B intersect with analysis channel portions 75A, 75B of microchip 6A. In preparing microchip 6A, the cover plate was bonded to the substrate over the etched channels by hydrolyzing the facing surfaces, bringing them into contact with each other, and heating the assembly at 500° C. Microchip 6A includes a side reservoir 80, a sample reservoir 85, a buffer reservoir 90, and a waste reservoir 95. The reservoirs are affixed with epoxy to the substrate at the point where the channels extend beyond the cover plate. Electrical connection between the high voltage power supply and the reservoirs is made using platinum wire connection as illustrated for the embodiment of FIG. 1B. Side channel portion 70A is filled with 10% (w/v) acrylamide that is polymerized to gel form in situ. The polymer allows ionic current to pass, but inhibits bulk fluid flow in the manner discussed above. The polymer extends to within about 1 mm of the intersection. The three remaining channel portions, 70B, 75A, and 75B are filled with a buffer solution to prevent polymerization of the acrylamide in those channel portions.

Working Example

Figure 6A:
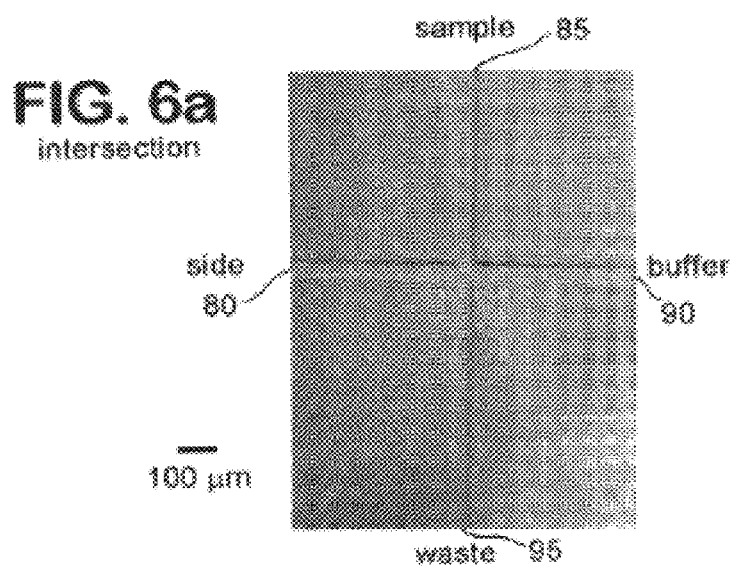
FIG. 6A is a white light image of the intersection portion of the fluid channels shown in FIG. 5.
Figure 6B:
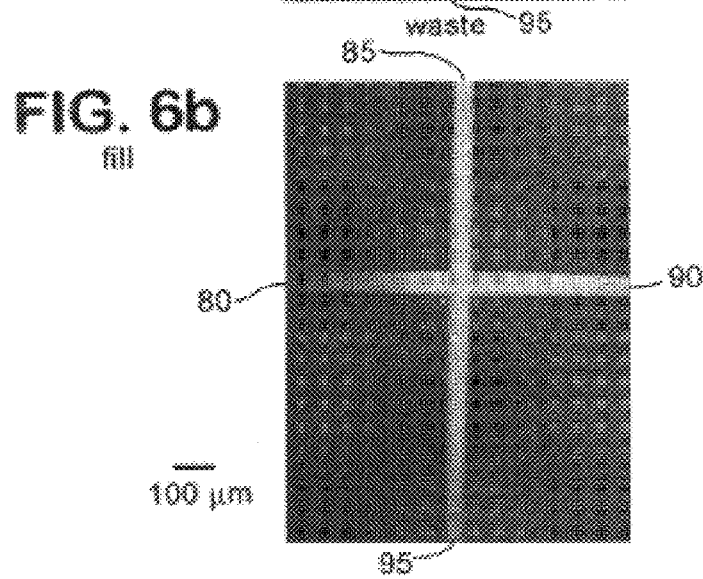
FIG. 6B is a fluorescence image showing the filling of the intersection portion of the fluid channels of FIG. 6A with rhodamine B buffer.
Figure 6C:
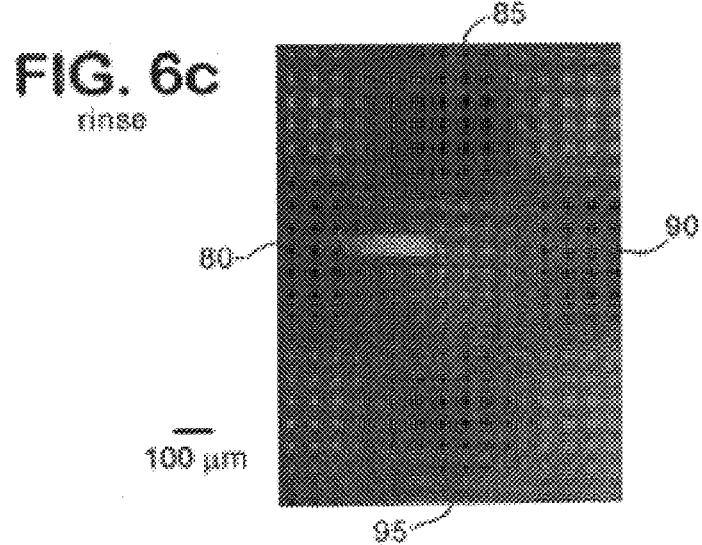
FIG. 6C is a fluorescence image showing the rinsing of the intersection of FIG. 6B with a buffer.

Referring now to FIG. 6A, there is shown an example of a microchip similar to that shown in FIG. 5. In FIG. 6A, the chip is backlit to show the microchannels and the intersection thereof. FIG. 6B, shows the intersection being filled with rhodamine B buffer by applying potentials of 1.0 kV and 0 kV to the sample reservoir 85 and side reservoir 80, respectively. Rhodamine B is pumped into the buffer channel 70B and waste channel 75B which are free of electric fields. In FIG. 6C the intersection is rinsed with a buffer solution by applying 1 kV, 0 kV, 0 kV, and 0 kV to the buffer reservoir 90, sample reservoir 85, side reservoir 80, and waste reservoir 95, respectively. A small amount of rhodamine B is left in the side channel due to a small dead volume. Because of the high electrical resistance of the polymer filled channel, the utilization of the applied electric potential for the electroosmotic pumping effect is not as efficient in this example as for the embodiments described previously herein. However, polymer plugs having a lower electrical resistance could be generated using plugs of different spatial extent or conductivity.

Additional Embodiments and Applications

Figure 7:
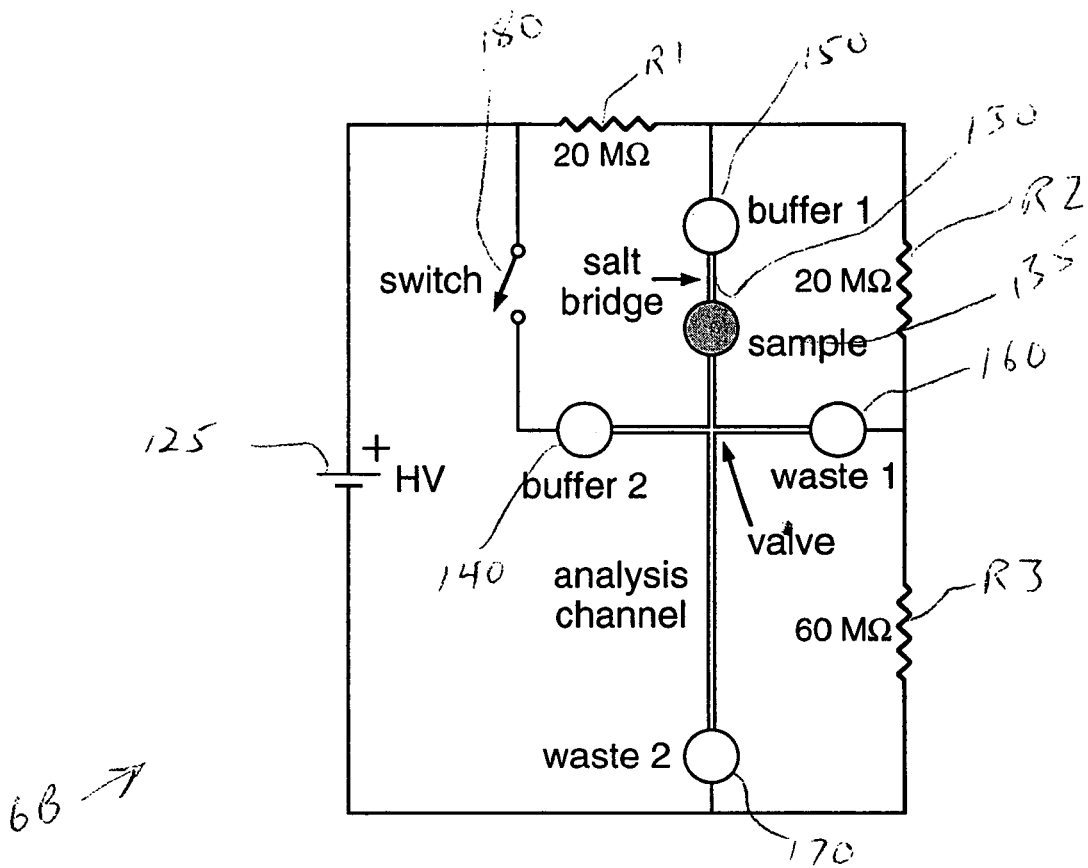
FIG. 7 is a schematic diagram of a further embodiment of a microchip according to this invention.

Referring now to FIG. 7, there is shown an arrangement for controlling sample loading and injection procedures which includes a microchip 6B according to the present invention. Microchip 6B includes a first buffer reservoir 150, a second buffer reservoir 140, a sample reservoir 135, a first waste reservoir 160, and a second waste reservoir 170. A high voltage source 125 is connected to the first buffer reservoir 150, the first waste reservoir 160, and the second waste reservoir 170 through a voltage dividing network consisting of resistors R1, R2, and R3. A switch 180 is connected between the high voltage source 125 and the second buffer reservoir 140. In the embodiment shown in FIG. 7, the high voltage source is not directly connected to the sample reservoir 135 as in the embodiment of FIG. 5. Instead, electrical connectivity is made through a small channel extending between the first buffer reservoir 150 and the sample reservoir 135. A bridging membrane 130 is formed in the microchannel between the first buffer reservoir 150 and the sample reservoir 135. The bridging membrane 130 is formed of a free solution or a polyacrylamide gel for the purpose of minimizing any electrochemically generated products in the sample material.

To perform injections, a variable volume valve is configured with 1.0 kV, 0.8 kV, 0.6 kV, and 0 kV applied to the second buffer reservoir 140, first buffer reservoir 150, first waste reservoir 160, and second waste reservoir 170. To inject a sample plug, the switch 180 is opened at the start of the injection period. This removes the electric potential at the second buffer reservoir 140 and continues to apply a potential to the first buffer reservoir 150, first waste reservoir 160, and second waste reservoir 170. At the end of the injection period, switch 180 is closed. The injection procedure of this embodiment is essentially identical to an embodiment where the high voltage is applied directly in the sample reservoir. However, it avoids to a large extent the problems associated with the electrochemical generation of undesired products in the sample material.

Figure 11:
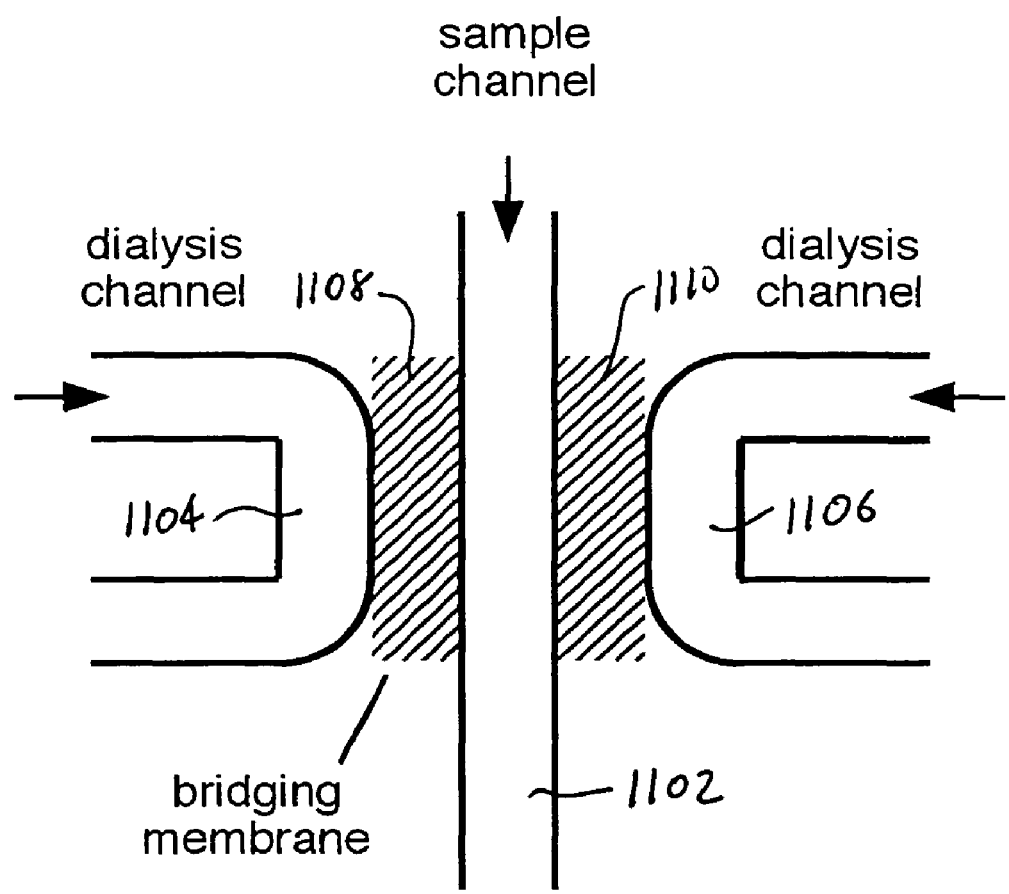
FIG. 11 is a schematic diagram of an arrangement of microchannels and bridging membranes in accordance with another aspect of this invention for accomplishing ionic or molecular separation of a fluidic material.

A second use of a bridging membrane according to the present invention is the separation of ions and/or molecules in a sample material based upon their properties such as charge, size, or a combination thereof. The microchip is fabricated with a sample channel and a dialysis or electrodialysis channel on one or both sides of the sample channel. A preferred embodiment of this application is shown schematically in FIG. 11. A sample channel 1102 is formed in fluid communication with a sample reservoir (not shown) and a waste reservoir (not shown). A first dialysis channel 1104 and a second dialysis channel 1106 are formed on opposite sides of the sample channel 1102. The dialysis channels 1104 and 1106 are separated from the sample channel 1102 by bridging membranes 1108 and 1110, respectively. A microchip embodiment of this arrangement is fabricated as described above with reference to the embodiment of FIG. 1. The sample material and dialysis buffer are transported through their respective channels using either electrokinetic transport or a hydraulic force. In addition, a potential difference can be applied between the sample and dialysis channels to cause or prevent the transport of ions through the bridging membranes 1108, 1110 from the sample channel 1102 to the dialysis channels 1104, 1106, respectively. In this manner, small ions or molecules are transported out of the sample channel for analysis or to remove them from the sample material in the sample channel 1102. Neutral small molecules can diffuse passively through the bridging membranes 1108, 1110 with or without an electric field present. Moreover, without a potential difference applied between the sample channel 1102 and the dialysis channels 1104, 1106, small ions diffuse passively across the bridging membrane. The efficiency of the dialysis process in this arrangement depends on dimensions of the sample channel, the dialysis channel(s), and the bridging membrane(s), the residence time of the sample material near the bridging membrane, and the magnitude of the electric potential applied between the sample and dialysis channels.

When an electrode material is in contact with water, reduction/oxidation reactions occur at the electrode surface producing hydrogen and/or oxygen gas. This gas evolution quickly leads to macroscopic gas bubble generation and can disrupt the current and electrokinetic flow especially in channels formed in glass or quartz substrates. In a further embodiment of a microchip according to this invention for generating pressure-driven flow by electroosmotic pumping a porous substrate is used with a metal film electrode. In this arrangement the bridging membrane conducts gas phase species rather than electrical current, but still inhibits bulk fluid transport. A working example of that arrangement was demonstrated using a polydimethylsiloxane (PDMS) substrate and a metal film for the ground electrode in one of the microfluidic channels. The PDMS acts as a bridging membrane that facilitates the removal of electrochemically generated gas phase species from the microfluidic channel because small gas phase molecules diffuse through the PDMS more rapidly than in glass. This greater diffusion allows chips formed with a PDMS substrate to be electrically contacted using a metal electrode at any point along a channel without the problem of macroscopic gas bubble formation in such a channel. Electrically contacting a microchip channel using this method enables the creation of an electric field-free region in the channel past the electrode, and materials can be pumped through this region using the pressure generated in the electroosmotic pumping region.

Figure 12:
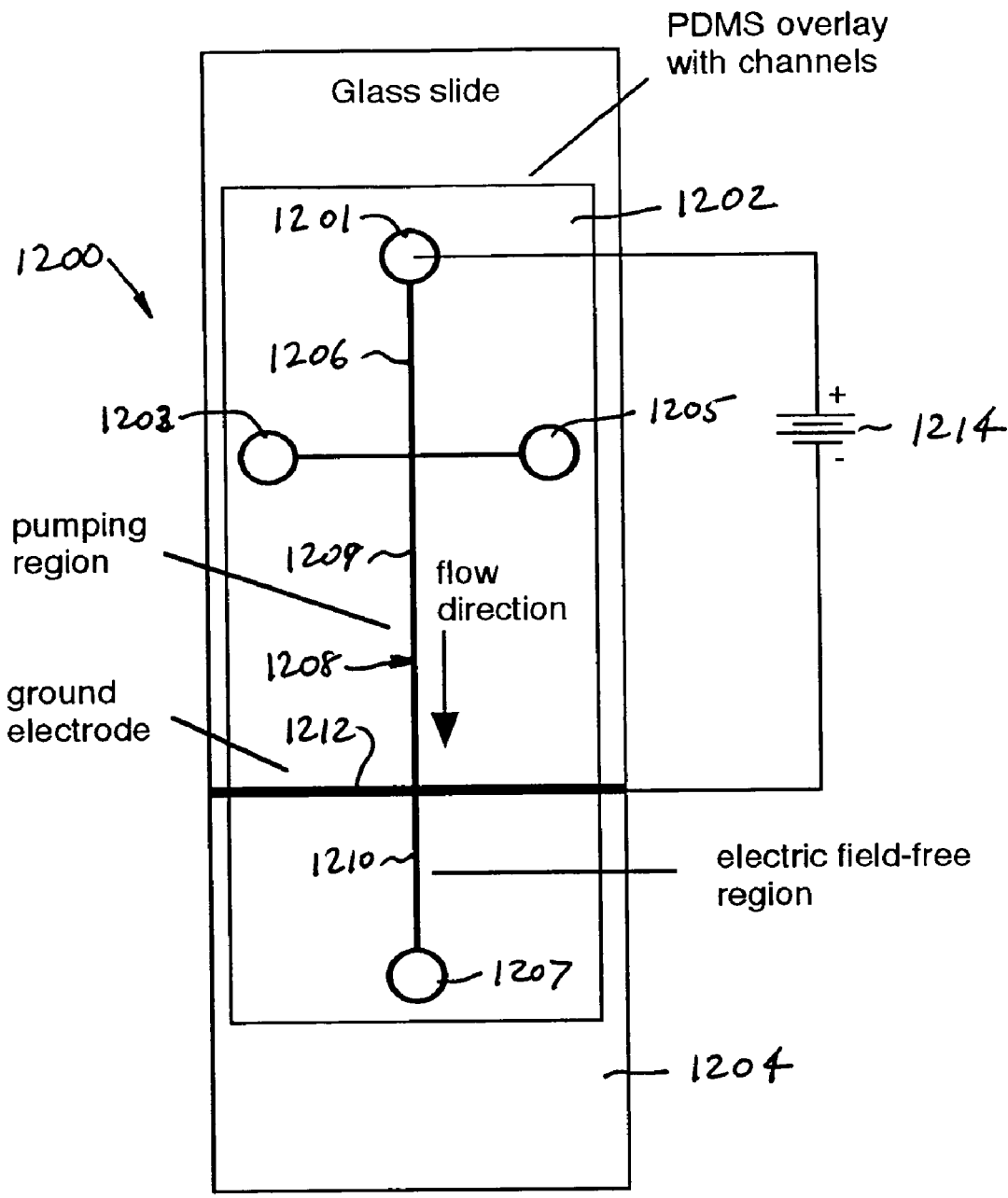
FIG. 12 is a schematic diagram of a microchip in accordance with a further aspect of this invention for effecting out removal of gas species generated in the fluidic materials when electrically energized.

To demonstrate this application, a hybrid microchip was fabricated using a PDMS substrate into which channels were molded and a glass cover plate on which metal electrodes were fabricated. The device 1200 is shown schematically in FIG. 12. The microchannel network includes a sample channel 1206, an analysis channel 1208, and a pair of side channels intersecting with the sample and analysis channels formed on a PDMS substrate 1202. To form the microchannel network on the PDMS substrate 1202, the PDMS material was polymerized in a negative silicon mold. The silicon mold was made by standard microfabrication techniques. Following polymerization, the PDMS substrate was removed from the silicon mold. A grounding electrode 1212 was formed by sputtering a chrome electrode pattern onto a glass substrate 1204. The glass substrate 1204 and the PDMS substrate 1202 were then oxidized and sealed together. The oxidation and sealing process used a plasma cleaner of a known type. Reservoirs 1201, 1203, 1205, and 1207 were formed in the PDMS substrate in fluid communication with the sample channel 1206, the analysis channel 1208, and the side channels, respectively.

Prior to use, the microchannels were rinsed with 1M NaOH and distilled water. This procedure was selected to minimize gas bubble formation when a large electric potential is used. Reservoir 1201 was filled with 1.0 μm diameter fluorescently labeled particles in a 20 mM SDS/10 mM HEPES buffer (pH 7.4). Reservoirs 1203, 1205, and 1207 were filled with buffer only, i.e., no particles. After filling the reservoirs, a electric potential was applied by connecting high voltage source 1214 between reservoir 1201 and the ground electrode 1212. No electric potential was applied to reservoirs 1203, 1205, or 1207. Under these conditions, the particles were transported out of reservoir 1201 toward the ground electrode 1212. The electroosmotic mobility of the bulk fluid was greater than the electrophoretic mobility of the anionic particles. Because the net velocity of the particles, i.e., the electroosmotic velocity of the bulk fluid minus the electrophoretic velocity of the anionic particles, was lower than the electroosmotic velocity, an increase in the average particle velocity was observed as the particles passed from the pumping region 1209 of analysis channel 1208, over the ground electrode 1212, and into the electric field-free region 1210 of analysis channel 1208. Particle velocities were measured before and after the ground electrode using time-lapsed fluorescence CCD imaging, and an electric field strength of 300 V/cm in the pumping region was used. The average particle velocity in the presence of the electric field was 0.7(±0.1) mm/sec (n=21) and in the field free region was 1.9(±0.6) mm/sec (n=7). A velocity increase of 2.6 times was seen as the particles passed over the ground electrode 1212 indicating termination of the electric field by the ground electrode. The electroosmotic mobility generated in the pumping region was estimated to be $6 \times 10^{-4}$ cm$^2$/(V·s) and corresponds to typical electroosmotic mobilities for native glass surfaces. Field strengths greater than 500 V/cm were successfully applied without macroscopic bubble generation.

The bridging membrane embodiment described above suggests a simplistic method for manufacturing fluidic microchips. The fluidic channels are molded as described above or embossed into a planar substrate using an embossing tool that contains the microfluidic channel design. After fabrication of the fluidic substrate a cover plate is formed from a gas porous material similar to that described above. In addition, the electrical contacts are formed on this coverplate material using metal deposition techniques to spatially pattern electrode structures in a desired layout. Other conducting materials besides metals could be used, e.g., conducting polymers, and different deposition or patterning methods could be used such as electrochemical deposition or silk screen patterning. The substrate and coverplate with electrodes are then bonded together using any of a number of approaches including adhesive bonding, covalent bonding, noncovalent bonding, or thermal bonding. The electrode layout provides electrical contact within channels and reservoirs as necessary in addition to electrical contact with the controlling power supply unit that drives the electrokinetic fluid manipulations. In addition the substrate or coverplate could have fluid reservoirs therein. This method of microchip fabrication could be extremely rapid and inexpensive.

Figure 13:
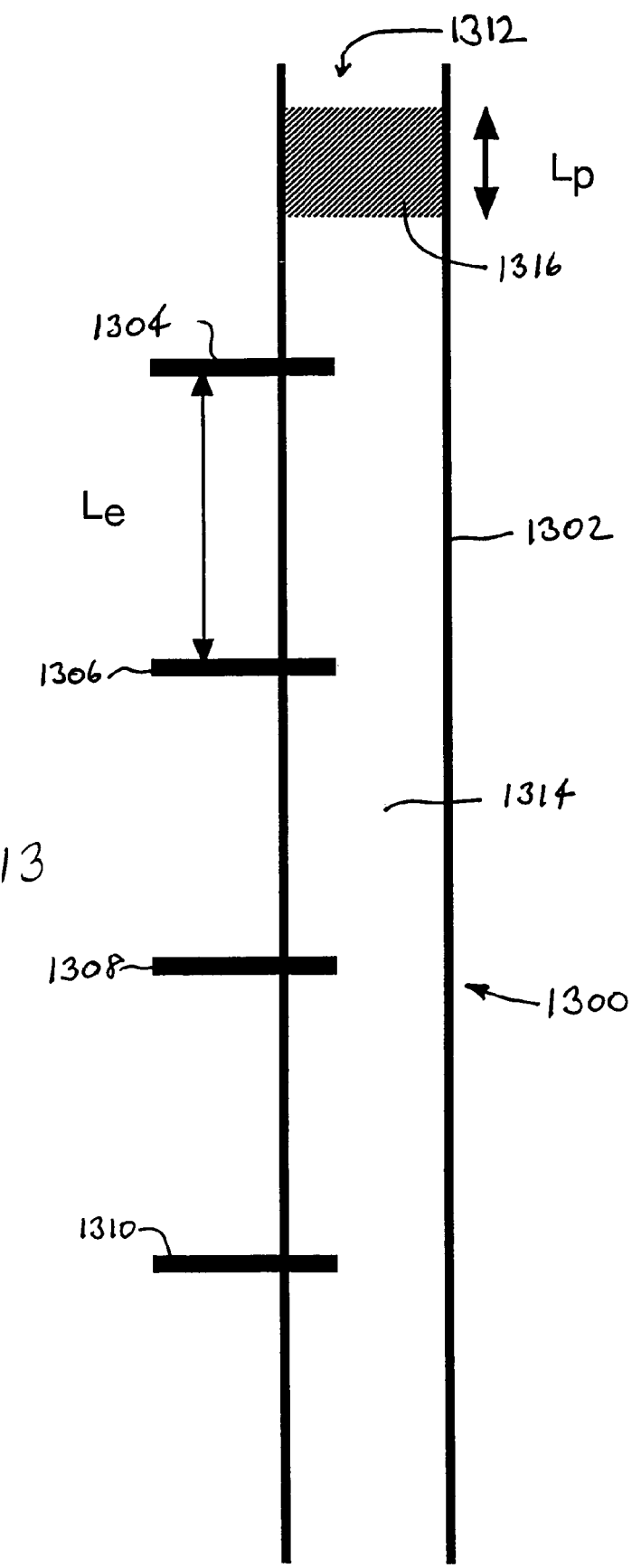
FIG. 13 is a schematic diagram of a microchannel according to another aspect of this invention having a series of bridging membranes for linearly transporting a material along the microchannel.

Shown schematically in FIG. 13 is another application of bridging membranes described above in a microchannel device according to this invention. The device 1300 has a substantially linear microchannel 1302 that has electrical contacts 1304, 1306, 1308, and 1310 disposed at spaced-apart locations along microchannel 1302. The distance $L_e$ between the electrical contacts is preferably fixed so that the contacts are equally spaced. However, it is not necessary to have equally spaced contacts, although such an arrangement is believed to be the most efficient design. The electrical contacts 1304, 1306, 1308, and 1310 are formed of a bridging membrane as described hereinabove with reference to FIG. 1. Alternatively, the electrical contacts can be made using the gas permeable membrane (PDMS) and metal electrode combination described above with reference to FIG. 12. The inlet 1312 of microchannel 1302 is adapted to access at least two different materials. Microchannel 1302 is predominantly filled with a first material 1314 that provides significant electroosmotic mobility. In operation, an electric potential is applied between electrodes 1304 and 1306 to induce electrokinetic transport of the first material toward electrode 1306. In that stage, electrodes 1308 and 1310 are left electrically floating. The inlet 1312 of microchannel 1302 is then brought into communication with a second material for a period of time to generate a plug of the second material 1316 that has an axial extent $L_p$. In the preferred use of device 1300, the second material is nonconducting or does not support electrokinetic transport. In the nonconducting case, the current through electrodes 1304 and 1306 is monitored so as to detect the arrival of the plug 1316 of the second material at electrode 1304. When a current drop is observed, an electric potential is applied between electrodes 1306 and 1308, leaving the others electrically floating. The electrokinetic force to transport material is now induced in microchannel 1302 between electrodes 1306 and 1308. The current through electrodes 1306 and 1308 is monitored. Upon arrival of the plug 1316 of the second material at electrode 1306 a reduction in current is detected at electrode 1306, and the voltage is applied between electrodes 1308 and 1310, while leaving the other electrodes floating. Again, when the plug 1316 of second material arrives at electrode 1308, a current drop occurs through that electrode. That signal resets the device so that the electrical potential is applied between electrodes 1304 and 1306, as in the initial state of operation. The maximum length of the plug 1316 of the second material is given by the following equation.

$$L_p < (-3)L_e$$

or for n=4, $L_p < L_e$. The minimum distance permitted between two separate plugs of the second material is $2L_e + L_p$. Device 1300 acts as a linear motor that is able to transport either a conducting or nonconducting material along microchannel 1302 by time dependent control of the electrical potentials applied to the series of electrical contacts 1304, 1306, 1308, and 1310.

Another application of a microfluidic device in accordance with this invention uses a plurality of bridging membrane contacts or electrodes as a pump for nonconducting liquids or gases. Such a pump uses a suitable electroosmotic liquid as a working fluid that would cycle repeatedly within the device with little if any loss. The combination of surface tension, vapor pressure, and electroosmotic forces is selected to be sufficient to withstand the pressure at the interface between the working fluid and the gas or liquid being evacuated. The maximum pumping pressure is attained when the electroosmotic flow is counterbalanced by the Poiseuille flow generated by the pressure drop, and depends on the axial electric field and the cross sections of the microchannels used. The vapor pressure of the working fluid is the ultimate limit of the vacuum that can be obtained with such a device. An embodiment of a cyclical pump utilizing this concept is described below.

FIGS. 14A to 14E are schematic diagrams of a two-cycle pump 1400 that is used as a vacuum pump in accordance with this aspect of the invention. The pump 1400 has an inlet 1401 that is connected to a chamber (not shown) to be evacuated. Pump 1400 includes an exhaust port 1402 that is open to the atmosphere and two channels 1404 and 1406 leading from the inlet port 1401 to the exhaust port 1402. Three electrodes 1408a, 1408b, and 1408c, preferably configured as bridging membranes, are disposed at several locations along channel 1404. Another electrode 1408d of similar construction is disposed at a preselected location on channel 1406. There is an additional electrical contact 1409 at the exhaust port 1402 that can be either a bridging membrane or another type of connection, such as a wire inserted in the exhaust opening. Electrical potentials V1, V2, V3, V4, and V5 are selectively applied to the electrodes 1408a, 1408b, 1408c, 1408d, and 1409, respectively, during the operation of the pump 1400. The following operating conditions are selected to provide the desired functionality. First, the voltage difference V4−V5 between the electrical contact 1409 and electrode 1408d and the voltage difference V1−V2 across the electrodes 1408a and 1408b are selected to produce axial electric fields in their respective channels that are sufficiently large to produce an electroosmotic pressure greater than the pressure difference between the exhaust port 1402 and inlet port 1401. The first condition (channel 1406) prevents the working fluid from entering the vacuum chamber during the exhaust stroke while the second condition (channel 1404) ensures that the working fluid can be displaced from the low pressure inlet to the high pressure exhaust. As a third condition, the net electroosmotic pressure produced by the voltage difference between electrodes 1408c and 1408b (V3−V2), between electrodes 1408a and 1408b (V1−V2), and between electrodes 1408c and 1409 (V3−V5) is selected to ensure flow in the counterclockwise direction during the exhaust stroke. The electric potential applied to electrode 1408c has a value V3 and the value of V3 that meets this third condition is $V3_{high}$. $V3_{high}$ is the value of V3 prior to the start of the intake stroke. The spacing between electrodes and the magnitudes of the applied voltages are selected to meet the above conditions.

Figure 14:
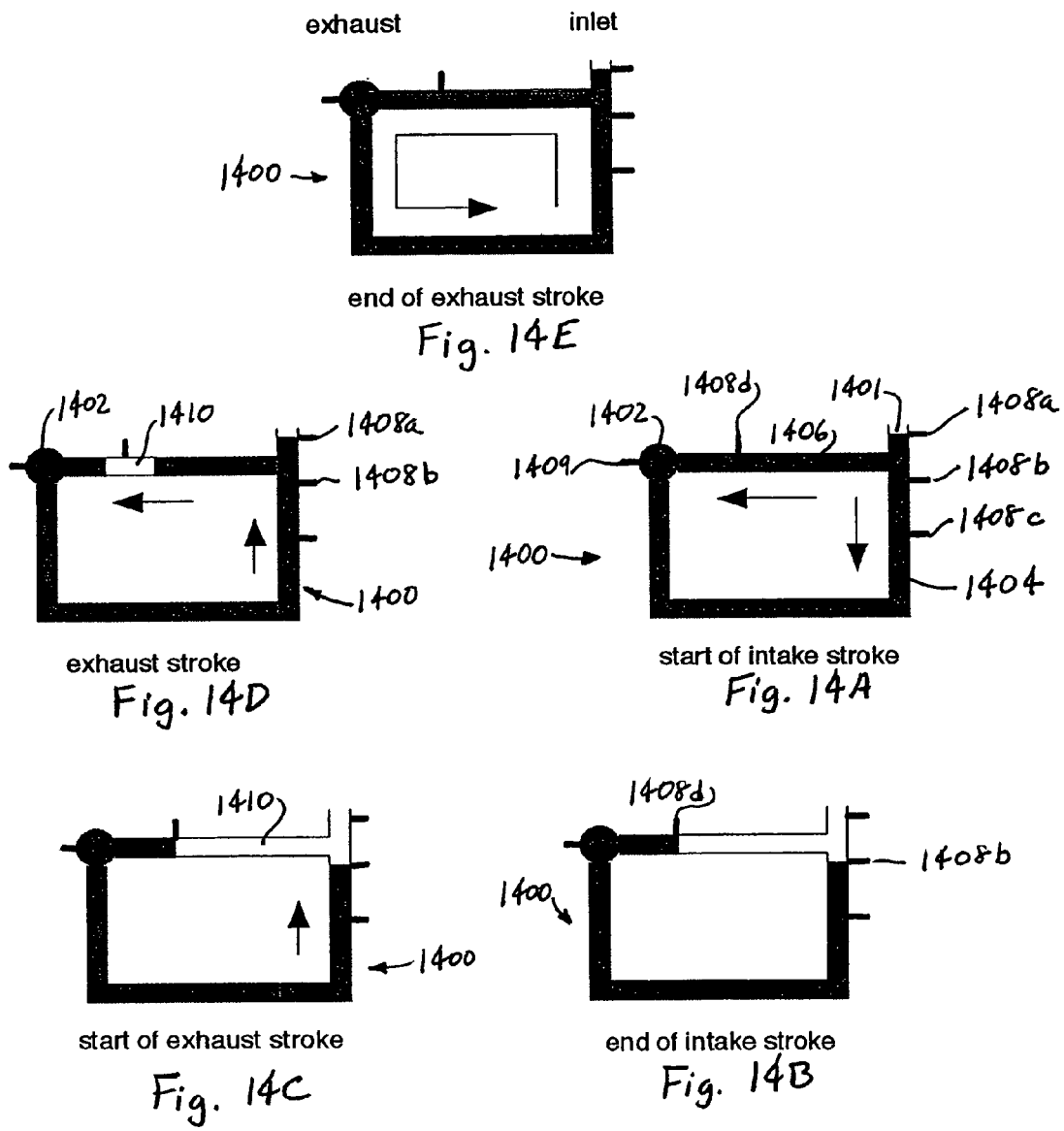
FIGS. 14A-14E are schematic diagrams showing the arrangement and operating sequence of a microfluidic vacuum pump utilizing bridging membranes.

The two strokes of the pumping cycle, intake and exhaust, are obtained by varying the voltage at electrode 1408c as shown in FIGS. 14A-14E. To start the intake stroke, the voltage at electrode 1408c is set equal to that at the exhaust port electrode 1409 as shown in FIG. 14A. The value of V3 at this stage is $V3_{low}$. Under that condition, the working fluid is pumped towards the exhaust port 1402 through both channels 1404 and 1406. The fluid flow stops when the gas-fluid interface in channel 1404 reaches electrode 1408b and the gas-fluid interface in channel 1406 reaches electrode 1408d as shown in FIG. 14B. Flow stops at this point because if the working fluid moved past those electrodes, the electrical conduction path in the channel would be broken and the electrical current driving the flow would be interrupted. At the end of the intake stroke, the portion of channel 1404 between the electrode 1408a and electrode 1408b is filled with gas at the pressure remaining in the vacuum chamber. Similarly, the portion of channel 1406 between the electrode 1408a and electrode 1408d is filled with gas at the pressure remaining in the vacuum chamber. The exhaust stroke is started by increasing the voltage at electrode 1408c to its initial value, $V3_{high}$, as shown in FIG. 14C. Because of the third condition identified above, the working fluid is electroosmotically pumped in a counterclockwise direction, driven by the voltage difference V3−V2, first filling channel 1404 up to electrode 1408a, where the interface is stopped because of the resumption of electrical current conduction between electrodes 1408a and 1408b as shown in FIG. 14D. The flow then continues towards the exhaust port 1402, pushing out the entrained gas 1410, which is now compressed to the exhaust pressure. Once electrical conduction is re-established between electrodes 1408d and 1409, FIG. 14E, the cycle can be repeated.

The pumping device according to this invention is not constrained to operate between vacuum and atmospheric pressure. Any liquid or gas that is immiscible with the working fluid and does not itself undergo electroosmotic flow can be pumped in this way. If the desired pumping speed cannot be attained at a given pressure differential with one channel, as described above, several channels could be connected in parallel between electrodes 1408a and 1409 to increase the capacity while maintaining the required pressure differential.

A still further application of a bridging membrane in accordance with another aspect of this invention relates to microfluidic valving. A microchannel network 1500 for implementing this application is shown schematically in FIG. 15. A plurality of microchannels 1501, 1503, 1505, and 1507 are interconnected at a common junction 1520. Reservoirs 1502, 1504, 1506, and 1508 are in fluid communication with the microchannels 1501, 1503, 1505, and 1507, respectively. Bridging membranes 1510, 1512, 1514, and 1516 are disposed at preselected locations along microchannels 1501, 1503, 1505, and 1507 between the reservoirs 1502, 1504, 1506, and 1508, respectively, and the common intersection 1520. Electrical potentials are selectively applied between the reservoirs 1502, 1504, 1506, and 1508 and their corresponding bridging membranes 1510, 1512, 1514, and 1516, respectively, to pump materials from the reservoirs through the fluidic microchannels.

In a first mode of operation, appropriate potentials are applied between reservoirs 1502 and 1508 and bridging membranes 1510 and 1516, respectively, to transport first and second materials from reservoirs 1502 and 1508, respectively, through channels 1501 and 1507 into the common intersection 1520. No potentials need be applied to reservoirs 1504 or 1506 or to bridging membranes 1512 or 1514. The first material is transported from channel 1501 into channel 1503, and the second material is transported from channel 1507 into channels 1503 and 1505. The electrical potential at reservoir 1508 is then removed or lowered relative to the electrical potential at reservoir 1502. This causes the first material to be transported into channel 1505. The electrical potential at reservoir 1508 is then returned to its initial value to terminate the transporting of the first material into channel 1505.

In a second mode of operation, first and second materials are drawn from their respective reservoirs into the common intersection instead of being pushed as in the first mode of operation. Appropriate potentials are applied between reservoirs 1504 and 1506 and bridging membranes 1512 and 1514, respectively, to draw the first and second materials from reservoirs 1502 and 1508, respectively, through channels 1501 and 1507 into the common intersection 1520. No electrical potentials need be applied to reservoirs 1502 and 1508 or to bridging membranes 1510 and 1516. As in the first mode of operation, the first material is transported from channel 1501 into channel 1503, and the second material is transported from channel 1507 into channels 1503 and 1505. The electrical potential at reservoir 1504 is removed or lowered relative to the electrical potential at reservoir 1506 to transport the first material into channel 1505.

The electrical potential at reservoir 1503 is then returned to its initial value to terminate the transporting of the first material into channel 1505.

Figure 15:
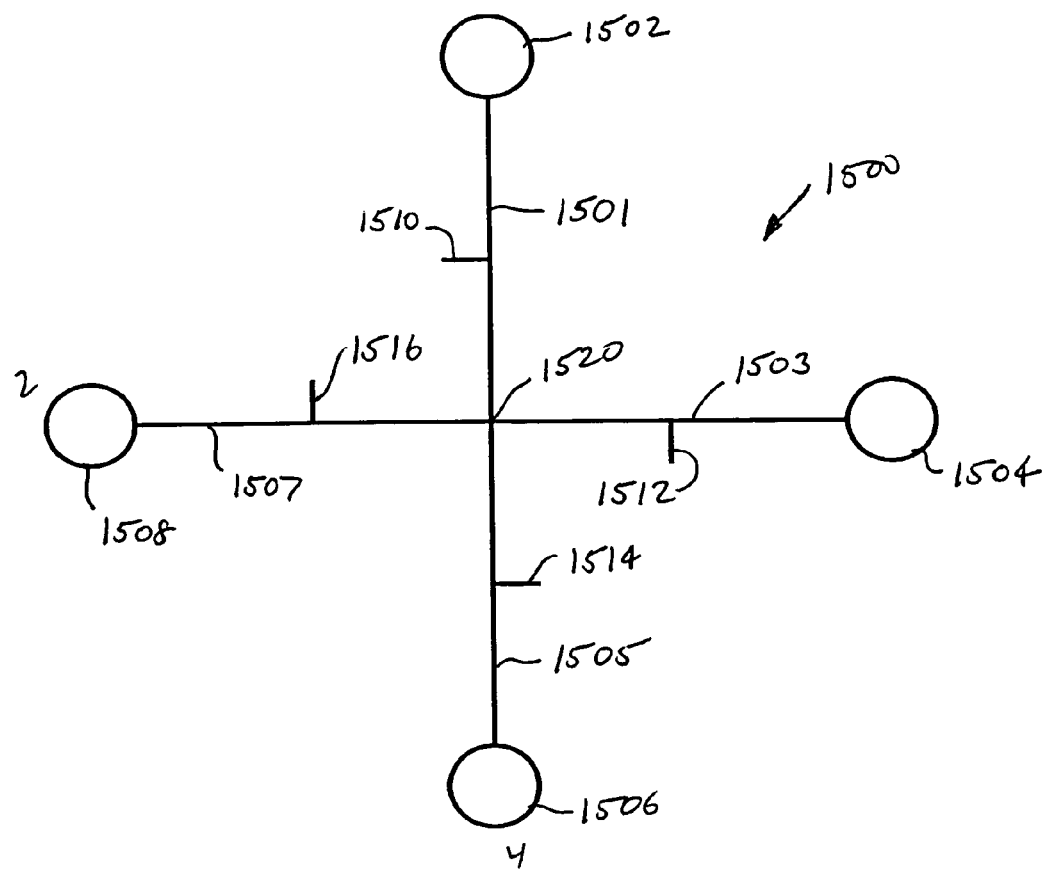
FIG. 15 is a schematic diagram showing a cross arrangement of microchannels and bridging membranes in accordance with a further aspect of this invention for accomplishing microfluidic valving of a fluidic material.

In both the first and second modes of operation of the microchannel network shown in FIG. 15, the electrical potentials at reservoirs 1508 and 1506 can be raised relative to the potentials at reservoirs 1502 and 1504 for the respective material dispensing schemes. Also, bridging membranes 1510 and 1516 or 1512 and 1514 can be connected to a common potential or ground. In the first mode of operation, reservoirs 1504 and 1506 can be combined into a single, common reservoir.

In a third mode of operation, appropriate electrical potentials are applied between reservoirs 1502, 1508, and 1506, and bridging membranes 1510, 1516, and 1514 such that first, second, and fourth materials are transported from reservoirs 1502, 1508, and 1506, respectively, through channels 1501, 1507, and 1505, respectively, into channel 1503. At equilibrium, the proportions of the first, second, and fourth materials in the common intersection 1520 are constant. In a variation of this mode of operation, the transporting of the first, second, and fourth materials can be accomplished by applying an appropriate electrical potential between reservoir 1504 and bridging membrane 1512, and having the channels 1501, 1503, 1505, and 1507 dimensioned appropriately. The second material is dispensed into channel 1505 by applying appropriate potentials between reservoirs 1508, 1504, and 1506 and bridging membranes 1516, 1512, and 1514, respectively. The dispensing of the second material into channel 1505 can be accomplished by applying an appropriate electrical potential between reservoir 1502 and bridging membrane 1510, and having channels 1501, 1503, 1505, and 1507 dimensioned appropriately. In addition, bridging membranes 1510, 1512, 1514, and 1516 can be connected to a common potential or to ground.

In any of the modes of operation described for the microchannel network 1500 shown in FIG. 15, the electrical potentials can be applied between any combination of reservoirs and corresponding bridging membranes to enhance or diminish the transport of material within the respective channel or channels.

Figure 16:
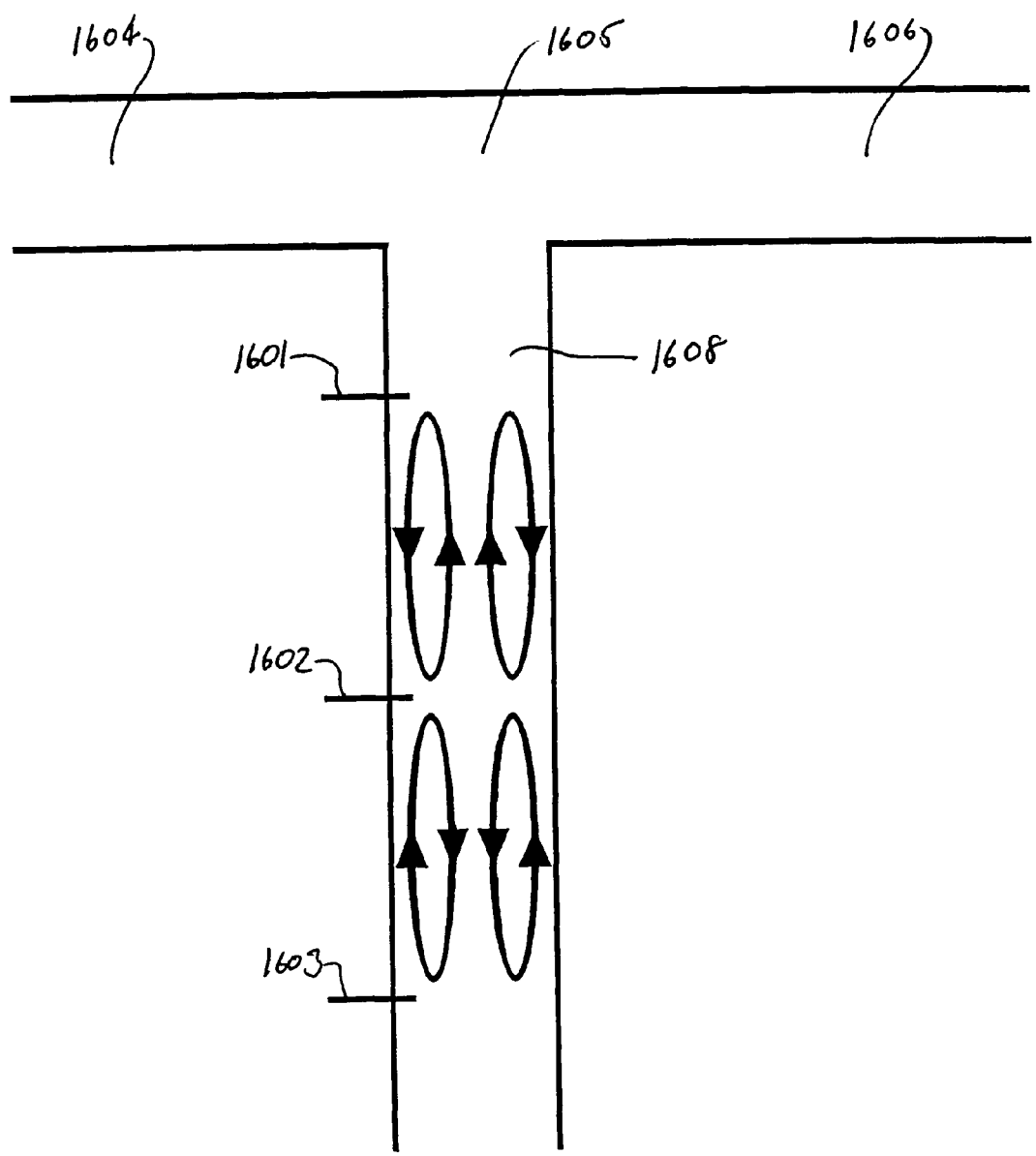
FIG. 16 is a schematic diagram of an arrangement of microchannels and bridging membranes in accordance with another aspect of this invention for mixing of fluidic materials.

Yet another microchannel arrangement employing bridging membranes in accordance with this invention is shown in FIG. 16. In this implementation a group of three bridging membranes 1601, 1602, and 1603 is used to provide mixing of materials that are supplied from a mixing tee 1605. A first material is supplied from microchannel 1604 and a different material is supplied from microchannel 1606. The first and second materials are electrokinetically transported through tee intersection 1605 into the mixing microchannel 1608 by applying appropriate voltages to channels 1604 and 1606 relative to channel 1608. The bridging membranes 1601, 1602, and 1603 are attached to channel 1608 so as to form three spatially distinct electrical contacts or electrodes. Voltages are applied to bridging membranes 1601 and 1603 relative to bridging membrane 1602 for generating opposing electrokinetic forces on the fluid which cause circulation patterns in the transported materials similar to those indicated by the arrows in FIG. 16. In practice, the fluid motion is three-dimensional with the flow near the channel walls being toward bridging membrane 1602 and the flow in the center of the channel being away from bridging membrane 1602. Materials are mixed in this fashion under either stopped flow or continuous flow conditions, i.e., the average net velocity of the materials in the channel 1608 being zero or non-zero, respectively. A series of such mixers could also be cascaded for enhanced mixing of the materials.

Figure 17:
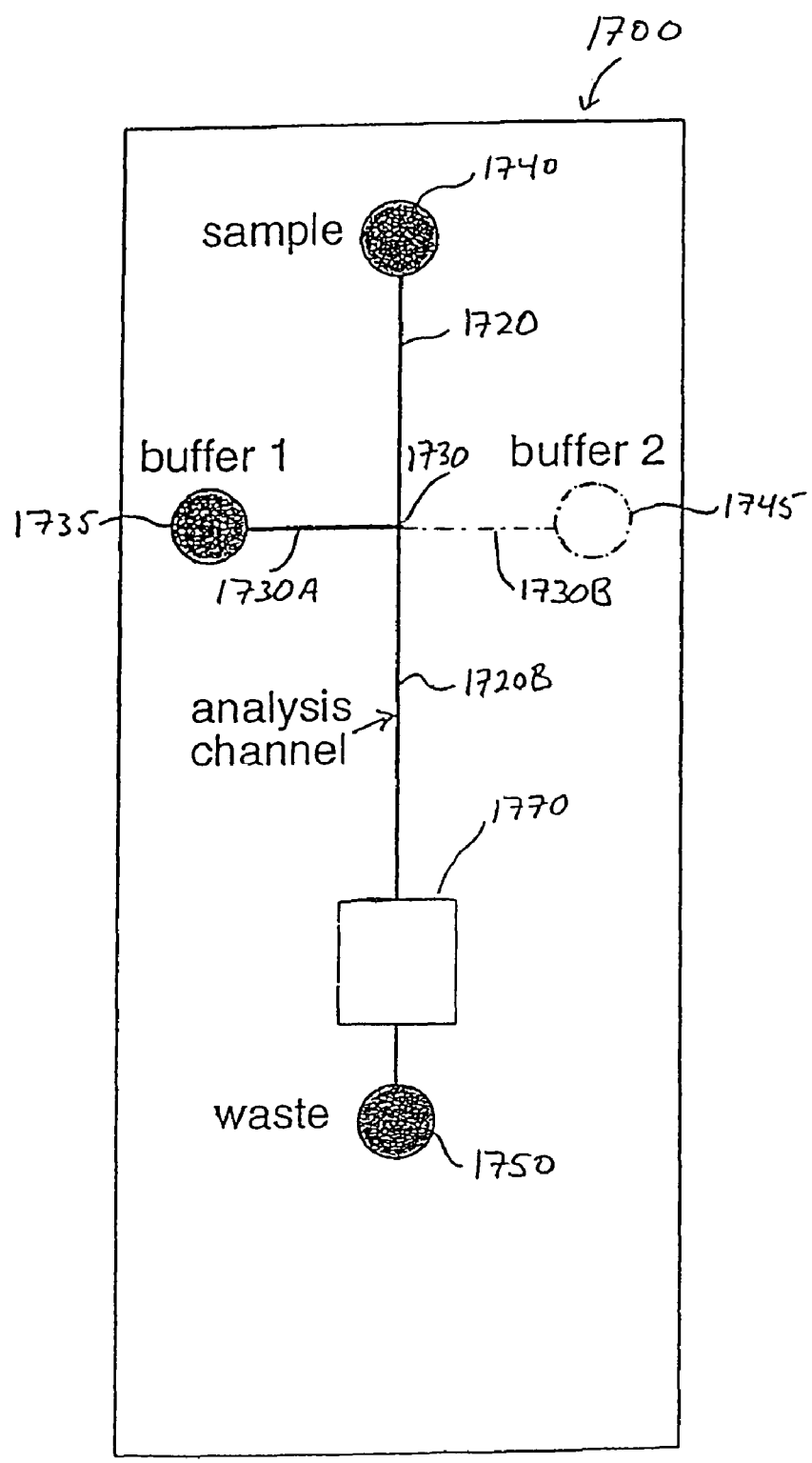
FIG. 17 is a schematic diagram of an arrangement of microchannels and pumping devices in accordance with another aspect of this invention for accomplishing focusing of a stream of fluidic material in a region of a microchannel which is uninfluenced by an electric field.

In accordance with another aspect of the present invention, a microfabricated device and method are provided for focusing a stream of fluid in at least one dimension and transporting the focused fluid stream within a channel of the microfabricated device which is uninfluenced by an electric field. A first configuration of such a device, microchip 1700, is illustrated in FIG. 17. The microchip 1700 has a sample channel 1720, a buffer channel 1730A, and an analysis channel 1720B formed therein. The microchip 1700 may be fabricated from materials and by methods as described above with respect to the microfabricated device of FIG. 1.

A sample reservoir 1740 is provided at a first end of the sample channel 1720 in fluid communication with the sample channel 1720. A first buffer reservoir 1735 is provided at a first end of the buffer channel 1730A in fluid communication with the buffer channel 1730A. The sample and buffer reservoirs 1740, 1735 supply materials for fluidic transport through the microfabricated channels. Optionally, additional buffer channels and reservoirs may be provided in the microchip 1700. For example, a second buffer channel 1730B may be provided in the microchip 1700 along with a second buffer reservoir 1745 in fluid communication with a first end of the second buffer channel 1730B.

The sample channel 1720 and buffer channels 1730A, 1730B intersect at channel junction 1730 to provide a region in which a stream of sample fluid can be focused. The buffer channels 1730A, 1730B are arranged relative to the sample channel 1720 such that the flow of buffer fluid through the buffer channels 1730A, 1730B into the channel junction 1730 focuses, or confines, a stream of sample fluid flowing into the channel junction 1730. For example, as illustrated in FIGS. 17, 24A, and 24B, the sample channel 1720 and buffer channels 1730A, 1730B intersect to form a cross intersection at channel junction 1730 so that the buffer channels 1730A, 1730B are disposed on opposing sides of the channel junction 1730 with the sample channel 1720 communicating with the channel junction 1730 at a location between the buffer channels 1730A, 1730B. As shown in FIG. 24B, the flow of buffer and sample fluid into the channel junction 1730 creates a confinement, or focusing, of the sample stream to a central region of the analysis channel 1720B, reducing the width of the sample stream in the channel junction 1730 and the analysis channel 1720B along a first transverse dimension. Alternatively, in the configuration where a single buffer channel 1730A and reservoir 1735 are provided, the flow of buffer and sample fluid into the channel junction 1730 creates confinement, or focusing, of the sample stream along the side of the analysis channel 1720B, as depicted in FIG. 24C. Confinement of the sample stream permits the volume of the sample stream to be reduced, so as to provide a smaller volume sample to a downstream detector to yield a potential increase in detector sensitivity.

To provide flow of sample fluid and buffer fluid from the respective reservoirs into the channel junction 1730 and analysis channel 1720B, a fluid transport device 1770 is provided downstream from the analysis channel 1720B. The fluid transport device 1770 functions to draw buffer material and sample material into the channel junction 1730 by creating a reduced hydraulic pressure at the fluid transport device 1770 relative to the pressure in the sample and buffer reservoirs 1740, 1735, 1745. The reduced pressure at the fluid transport device 1770 causes both buffer material and sample material to be drawn from the respective reservoirs 1735, 1745, 1740 into the channel junction 1730. A waste reservoir 1750 may be provided to receive fluid that exits from the fluid transport device 1770.

The fluid transport device 1770 may include any structure suited to creating electroosmotic transport of biological or chemical materials within the channels of the microchip 1700. The dimensions, e.g., length, width, and depth, of the buffer channels 1730A, 1730B and sample channel 1720 are selected to provide the desired flow of the material through each of the buffer and sample channels 1730A, 1730B, 1740, so that the desired focusing of the sample material is achieved. Provision of a fluid transport device 1770 downstream from the analysis channel 1720B permits confinement of the sample stream in an electric field free region at the channel junction 1730 and analysis channel 1720B.

Figure 18:
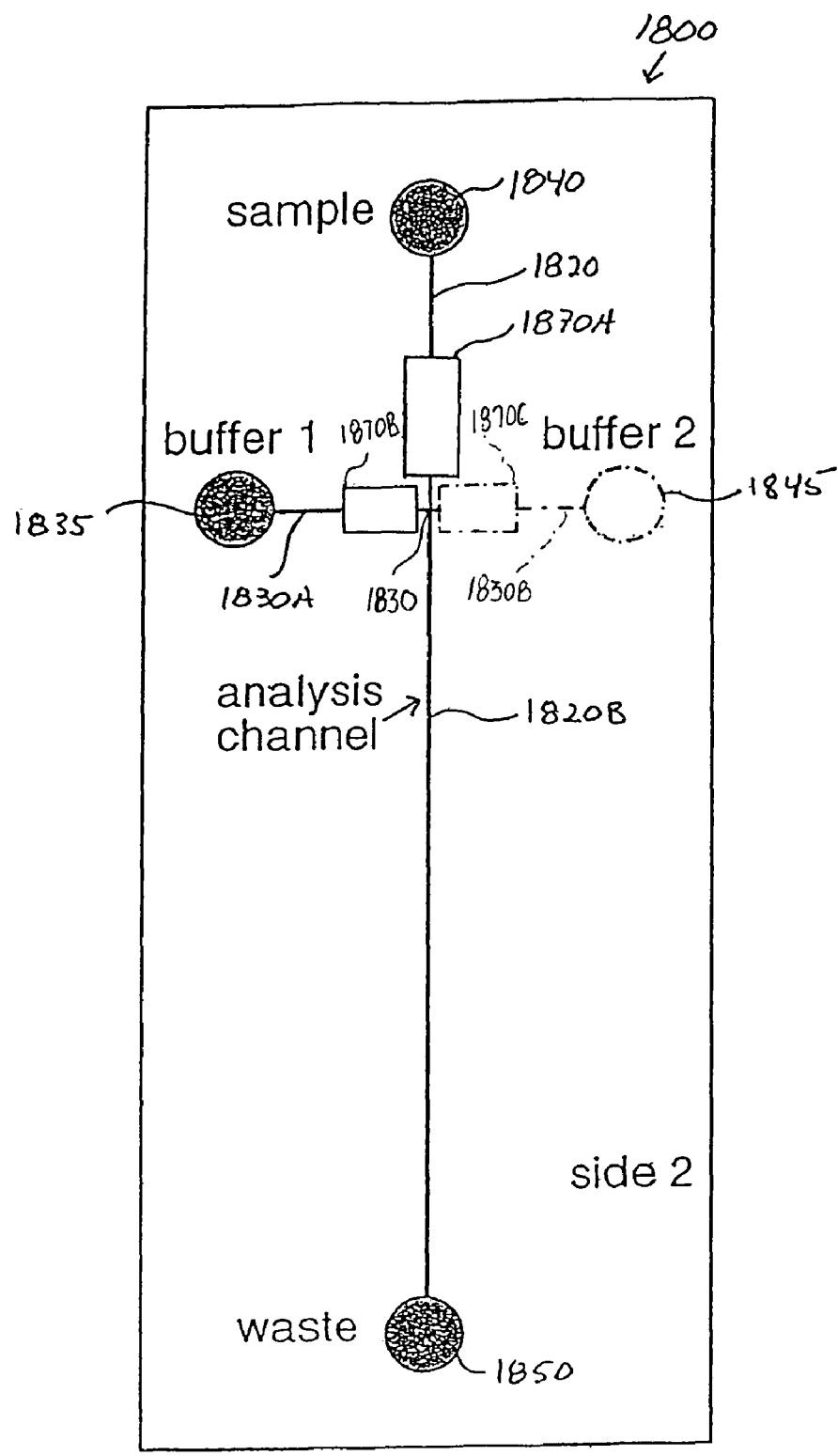
FIG. 18 is a schematic diagram of a further arrangement of microchannels and pumping devices for accomplishing focusing of a stream of fluidic material in a region of a microchannel which is uninfluenced by an electric field.

In an alternative configuration, as illustrated in FIG. 18, the fluid transport device is disposed upstream from the channel junction 1830. Such a configuration also permits confinement and analysis of the sample stream in an electric field free region. As with the microchip 1700 of FIG. 17, the microchip 1800 of FIG. 18 comprises a sample channel 1820, a first buffer channel 1830A, an optional second buffer channel 1830B, and an analysis channel 1820B therein. Likewise, a sample reservoir 1840 is provided at a first end of the sample channel 1820 in fluid communication with the sample channel 1820. Buffer reservoirs 1835, 1845 are also provided at first ends of the respective buffer channels 1830A, 1830B in fluid communication with the respective buffer channels 1830A, 1830B. A waste reservoir 1850 is optionally provided to receive fluid from the analysis channel 1820B. The sample channel 1820 and buffer channels 1830A, 1830B intersect at channel junction 1830 to provide a region in which a stream of sample fluid can be focused in a similar fashion to the analogous structures in microchip 1700 of FIG. 17. Separate fluid transport devices 1870A, 1870B, 1870C are disposed along each of sample channel 1820 and buffer channels 1830A, 1830B, respectively. The dimensions of sample channel 1820 and buffer channels 1830A, 1830B are selected with regard to the pumping configuration. Accordingly, since the pumping configuration used in microchip 1800 differs from that used in microchip 1700, the dimensions of the sample channel 1820 and buffer channels 1830A, 1830B in microchip 1800 may differ from the length and width of the corresponding channels in the microchip 1700.

The fluid transport devices 1870A, 1870B, 1870C function to draw buffer material and sample material into the sample channel 1820 and into buffer channels 1830A, 1830B, respectively, and create an increased hydraulic pressure in the sample and buffer channels 1820, 1830A, 1830B relative to the channel junction 1830. Materials so drawn into the sample channel 1820 and buffer channels 1830A, 1830B flow into the channel junction 1830 so that focusing of the sample stream may be effected. The fluid transport devices 1870A, 1870B, 1870C may include any structures suited to creating electroosmotic transport of biological or chemical materials within the channels of the microchip 1800.

Figure 19A:
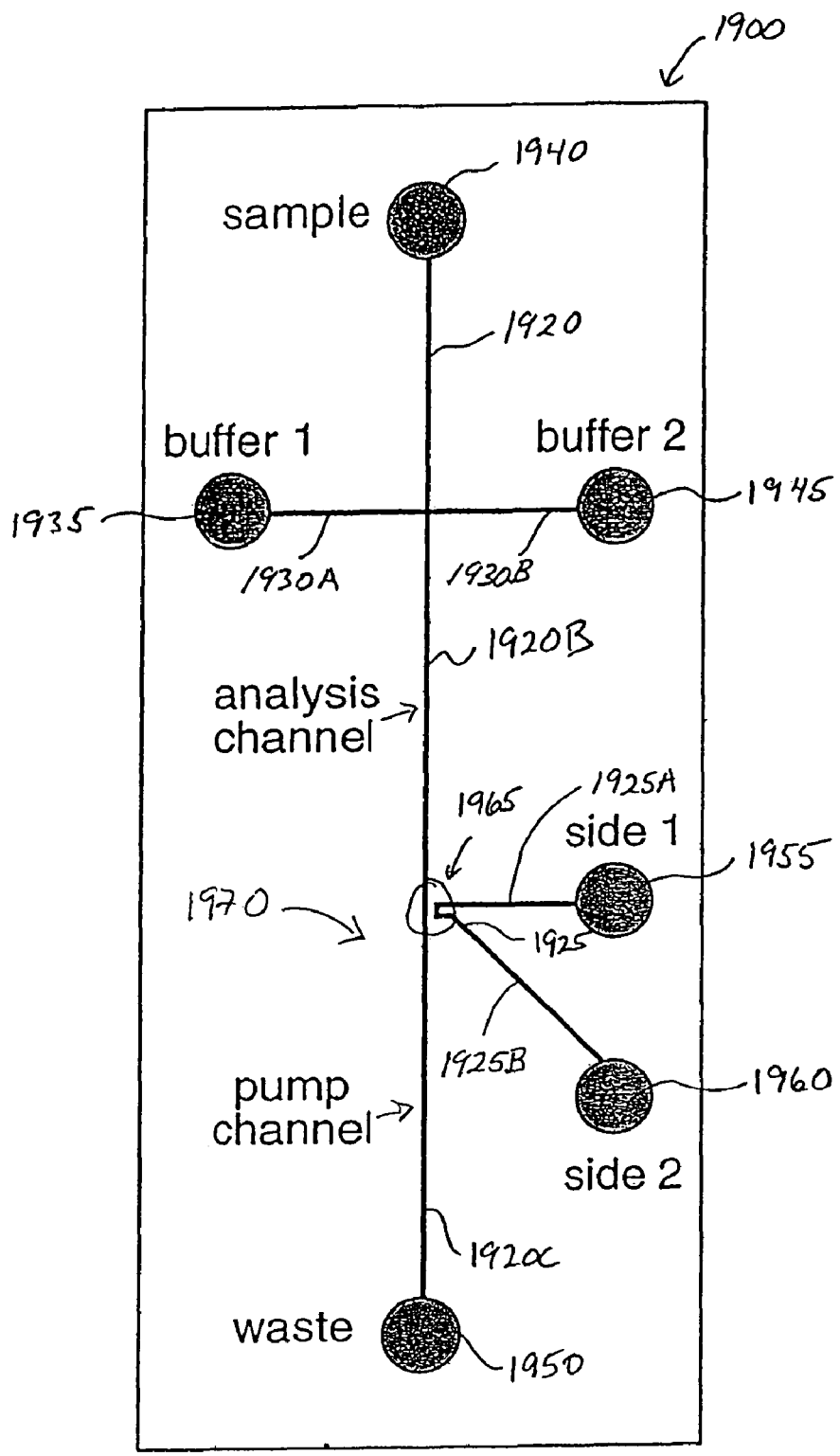
FIG. 19A is a schematic diagram of a first arrangement of microchannels and a bridging membrane for accomplishing focusing of a stream of fluidic material in a region of a microchannel which is uninfluenced by an electric field.

For example, the fluid transport devices of either microchip 1700 or microchip 1800 may take the form of a bridging membrane junction. A bridging membrane junction 1965 for use as the fluid transport device 1970 in a downstream pumping configuration in accordance with microchip 1700 is illustrated in FIG. 19A. The microchip 1900 comprises a similar configuration of reservoirs and buffer, sample, and analysis channels as that depicted in FIG. 17, where 1900-series reference numerals are used in FIG. 19A to denote features corresponding to those labeled with 1700-series reference numerals in FIG. 17. In addition, a fluid transport device is provided comprising a bridging membrane junction 1965, adjacent side channels 1925A, 1925B, and pump channel 1920C. The bridging membrane junction 1965 and side channels 1925A, 1925B correspond to the bridging membrane junction 65 and side channels 25A, 25B, respectively, described above with respect to FIG. 1 and may be fabricated and configured in a similar manner. Likewise, first and second side reservoirs 1955, 1960 are provided in communication with the respective side channels 1925A, 1925B in corresponding fashion to the side reservoirs 55, 60 of the microchip of FIG. 1. The fluid transport device 1970 functions to draw sample and buffer material into the analysis channel 1920B by electroosmotic flow in the pump channel 1920C between bridging membrane 1965 and waste reservoir 1950, by generating a sub-ambient pressure at the bridging membrane 1965, as illustrated in the following working example.

Working Example

A working example in accordance with the configuration of FIG. 19A was fabricated using standard photolithographic techniques. A photomask was fabricated by sputtering a chromium film (50 nm thick) onto a glass slide, spinning a positive photoresist (Shipley 1811) onto the chrome film, and exposing the microchip design into the photoresist using a CAD/CAM laser machining system (Ar$^+$, 457 nm). Subsequently, the metal film was etched with a solution of $CeSO_4/HNO_3$. The channel design was then transferred onto the glass substrate using a positive photoresist and a UV flood exposure. Following developing of the photoresist, the channels were etched into the substrate in a dilute, stirred $HF/NH_4F$ bath. Channel access holes of 3.5 mm diameter were drilled in the cover plate. To form the closed network of channels, the cover plate was bonded to the substrate over the etched channels by hydrolyzing both surfaces, bringing the cover plate into contact with the substrate, and annealing to 500° C. Cylindrical glass reservoirs were then affixed on the cover plate using epoxy. The channels were approximately 40 μm wide at half-depth and 9 μm deep. The microchip channel lengths that were used are listed in Table 1.

TABLE 1

Microchip channel lengths

| Channel | Length (mm) |
|---|---|
| sample | 8.1 |
| buffer 1 | 4.1 |
| buffer 2 | 4.3 |
| analysis | 10.1 |
| pump | 9.6 |
| side 1 | 4.4 |
| side 2 | 6.4 |

The output of a single programmable high voltage power supply (10A12-P4, Ultravolt) was applied to the side 1 reservoir 1955 with the waste reservoir 1950 grounded. Input to the power supply was computer controlled using a multifunction I/O card (NB-MIO16XL-42, National Instruments) and Labview 4.1 (National Instruments).

Fluid manipulations were monitored by fluorescence detection using rhodamine B as the sample (20 μM in 10 mM sodium tetraborate buffer, Exciton). The buffer in the buffer reservoirs 1935, 1945 and the first and second side reservoirs 1955, 1960 was 10 mM sodium tetraborate (pH 9.2). Two dimensional (2D) images were acquired using an inverted optical microscope (TE300, Nikon) equipped with a high pressure Hg lamp and a CCD camera (Princeton Instruments).

Figure 20A:
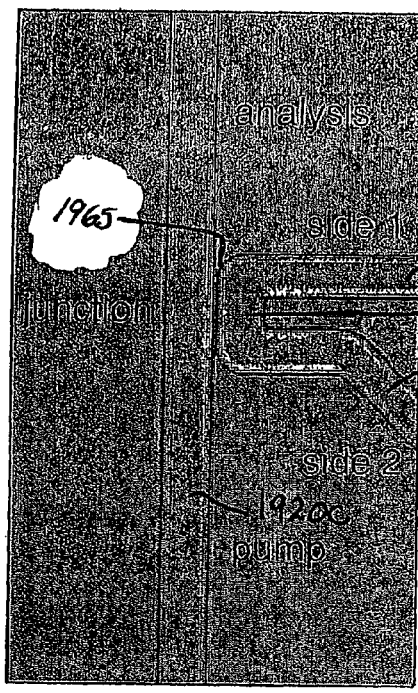
FIG. 20A is a white light image of the bridging membrane of FIG. 19A in accordance with the present invention.

The microchip 1900 included a bridging membrane junction 1965 to act as a junction to make an electrical connection to the analysis channel 1920B through the side channel 1925. The microchip 1900 was designed to have the analysis channel 1920B in close proximity to the side channel 1925, but not overlapping. The distance between the analysis channel 1920B and the side channel 1925 can be varied depending on the etch time for the analysis and side channels. The glass substrate etches isotropically so the longer the etch, the closer the analysis and side channels come to connecting. Using a stylus-based surface profiler, the bridging membrane junction 1965 between the analysis/pump channels 1920B, 1920C and the side channel 1925 was measured to be about 1 μm, as shown in FIG. 20A. Most bridging membrane junctions for these experiments were 1-10 μm wide.

Figure 20B:
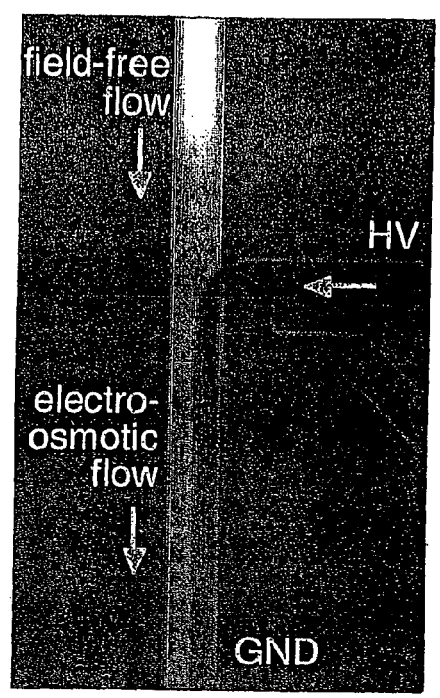
FIG. 20B is a fluorescence image of rhodamine B buffer drawn from the sample reservoir through the analysis channel by the pump channel of the microchip in FIG. 19A.

FIG. 20A shows a white light image of the junction fabricated as described above. FIG. 20B shows a fluorescence image of a sample (an organic dye, rhodamine B) being drawn from the sample reservoir 1940 through the analysis channel 1920B by the pump channel 1920C when a potential of 3 kV was applied to the side 1 reservoir 1955 and the waste reservoir 1950 was grounded. Also, buffer flow from the side 1 channel 1925A was observed moving through the bridging membrane junction 1965 into the pump channel 1920C. Accordingly, the pumping in FIG. 20B was about 50% efficient. The electroosmotic flow in the pump channel 1920C was greater than the electroosmotic flow through the bridging membrane junction 1965. The difference in flow rates was made up by drawing fluid into the pump channel 1920C from the analysis channel 1920B, which in turn drew fluid from the sample and buffer channels 1920, 1930A, 1930B into the analysis channel 1920B, as seen in FIG. 24B. As a result an electric field free pumping in the sample, buffer, and analysis channels 1920, 1930A, 1930B, 1920B was achieved.

FIG. 24A shows a white light image of the cross intersection on the microchip 1900. FIG. 24B shows a fluorescence image of the sample being focused by buffer streams from the buffer 1 and buffer 2 channels 1930A, 1930B, where the arrows indicate the direction of net flow. The buffer 1, buffer 2, and sample channels 1930A, 1930B, 1920 were 4.1, 4.3, and 8.1 mm in length, respectively, (Table 1) and had the same cross sectional area. These dimensions yielded about a 40% flow from each buffer channel 1930A, 1930B and about 20% flow from the sample channel 1920 into the analysis channel 1920B. As seen in FIG. 24B, the sample stream was spatially confined by the two buffer streams. The focusing region at the cross intersection was electric field free, because electric potentials were only applied between the side 1 reservoir 1955 and waste reservoir 1950.

The electrical potential could be applied to the side 1 reservoir 1955 and/or side 2 reservoir 1960 with the waste reservoir 1950 grounded to effect pumping. Also, the side 1 and side 2 channels 1925A, 1925B could be filled with polymer to assist in minimizing the electroosmotic flow through the bridging membrane junction 1965 into the pump channel 1920C. In the device above, the cover plate was thermally bonded to the substrate. In other experiments, the cover plate was bonded to the substrate using sodium or potassium silicate as an adhesive.

Figure 19B:
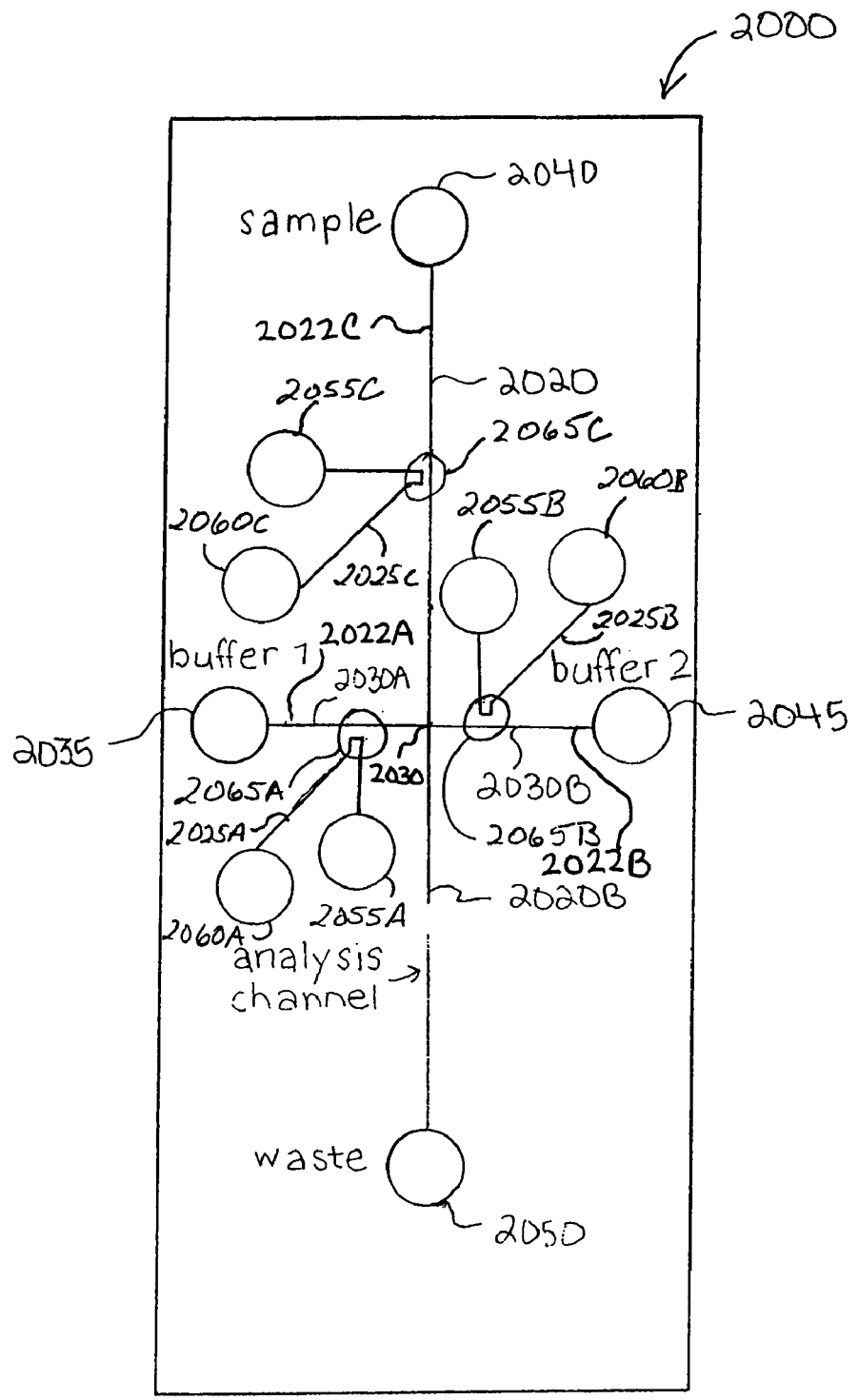
FIG. 19B is a schematic diagram of a second arrangement of microchannels and bridging membranes for accomplishing focusing of a stream of fluidic material in a region of a microchannel which is uninfluenced by an electric field.

Returning to the configuration of FIG. 18, bridging membranes may be used as the fluid transport devices 1870A, 1870B, 1870C, as illustrated in the microchip 2000 of FIG. 19B. The microchip 2000 comprises a similar configuration of reservoirs and buffer, sample, and analysis channels as that depicted in FIG. 18, where 2000-series reference numerals are used in FIG. 19B to denote features corresponding to those labeled with 1800-series reference numerals in FIG. 18. e.g., sample channel 2020, first buffer channel 2030A, second buffer channel 2030B, and waste reservoir 2050. In addition, fluid transport devices are provided in the form of bridging membrane junctions 2065A-C, adjacent side channels 2025A-C, and pump channels 2022A-C. The bridging membrane junctions 2065A-C and adjacent side channels 2025A-C are similar in construction to the bridging membrane junction 65 and side channels 25A, 25B described above with respect to FIG. 1 and may be fabricated and configured in a similar manner. Likewise, first and second side reservoirs 2055A-C, 2060A-C are provided in communication with each end of a respective side channel 2025A-C in corresponding fashion to the side reservoirs 55, 60 of the microchip of FIG. 1. Appropriate electrical potentials are applied between the sample and buffer reservoirs 2040, 2035, and 2045 and respective side reservoirs 2055A-C so that an increased pressure is created at the bridging membranes 2065A-C relative to the respective buffer and sample reservoirs 2035, 2045, 2040 to cause the sample and buffer materials to be transported by electroosmotic flow from the sample and buffer reservoirs 2040, 2035, 2045 through the pump channels 2022A-C into the channel junction 2030.

Figure 21:
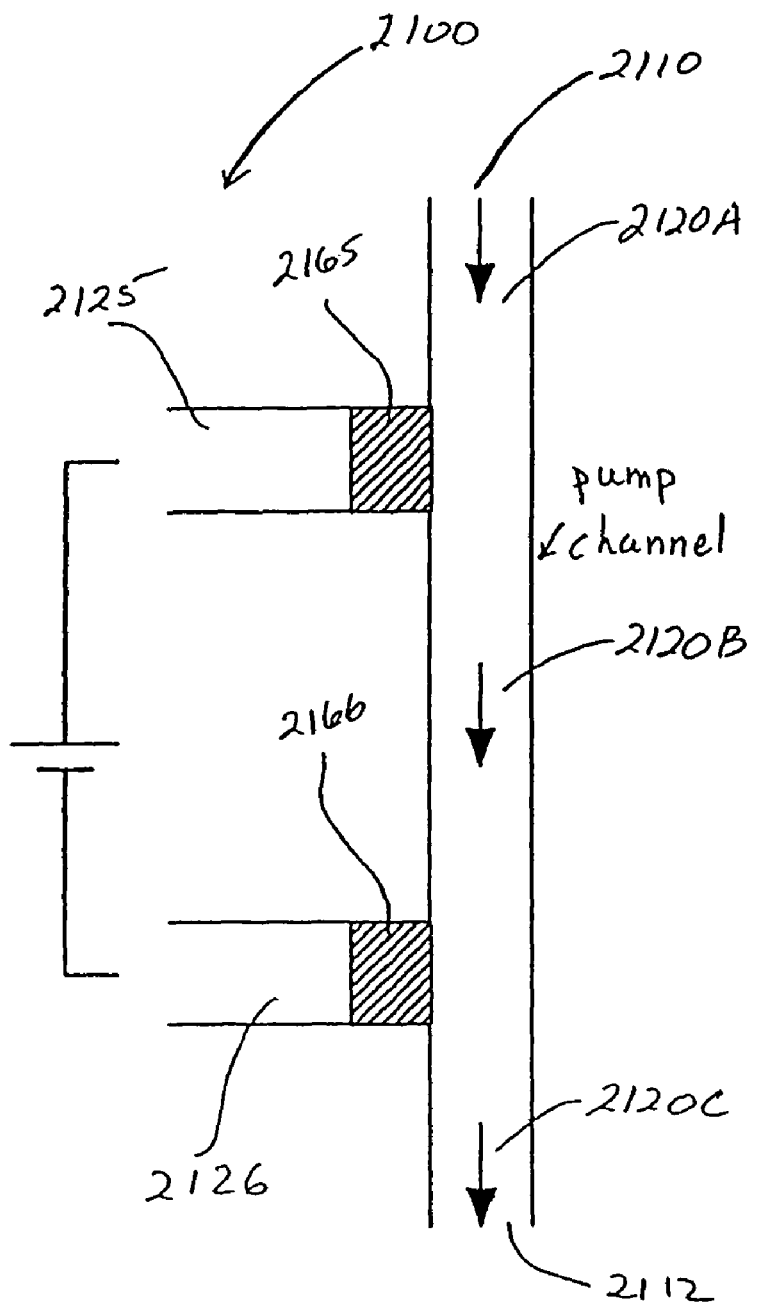
FIG. 21 is a schematic diagram of a pumping device comprising two bridging membranes for linearly transporting a material along a microchannel.

Referring now to FIG. 21, an alternative fluid transport device 2100 is illustrated which may be used as the fluid transport device 1770, 1870 in the microchip 1700 of FIG. 17 or the microchip 1800 of FIG. 18. The fluid transport device 2100 comprises an upper channel 2120A, a lower channel 2120C, and a pump channel 2120B communicating in end-to-end fashion to form a continuous channel 2120. A first side channel 2125 is provided adjacent the upper channel 2120A and communicates electrically with the pump channel 2120B through a first membrane 2165. A second side channel 2126 is provided adjacent the lower channel 2120C and communicates electrically with the pump channel 2120B through a second membrane 2166. The first membrane 2165 is disposed between the upper channel 2120A and first side channel 2125, as shown in the microfabricated device of FIG. 1. Similarly, the second membrane 2166 is disposed between the lower channel 2120C and second side channel 2126, as shown in the microfabricated device of FIG. 1. Alternatively, the first membrane 2165 can be fabricated in the first side channel 2125, in the same manner as the devices illustrated in FIGS. 5 and 10. The first and second membranes 2165, 2166 conduct electric current but inhibit, minimize, or reverse bulk fluid transport therethrough.

A potential is applied between the first side channel 2125 and the second side channel 2126, which generates electroosmotic flow in the pump channel 2120B in a direction away from the first membrane 2165 and toward the second membrane 2166. The volumetric fluid flow rate through the first and second membranes 2165, 2166 into the respective first and second side channels 2125, 2126 is lower than in the pump channel 2120B. The electroosmotic flow through the first and second membranes 2165, 2166 is ideally zero, but a reduction compared to that in the pump channel 2120B is sufficient. As a result, a negative pressure relative to the ends 2110, 2112 of the channel 2120 is generated on the pump channel side of the first membrane 2165, and a positive pressure relative to the ends 2110, 2112 of the channel 2120 is generated on the pump channel side of the second membrane 2166. Because a negative pressure is present on the pump channel side of the first membrane 2165, fluid material is drawn from the upper channel 2120A in the direction toward the first membrane 2165. Further, because a positive pressure is present on the pump channel side of the second membrane 2166, the fluid material is pushed into the lower channel 2120C in the direction away from the second membrane 2166. This configuration allows pumping of material from the upper channel 2120A into the lower channel 2120C. No electric fields are present in the lower and upper channels 2120C, 2120A. Arrows show the direction of net fluid flow. The arrangement shown in FIG. 21 is a subset of the arrangement shown in FIG. 13. Pump channel 2120B can be filled with a porous material or polymer that supports electroosmotic flow or can be fabricated with an array of nanochannels. Such configurations provide higher back pressures and can be used in higher pressure applications.

For example, an alternative fluid transport device 2700, similar to the fluid transport device 2100 of FIG. 21, but comprising arrays of nanochannels is depicted FIG. 27. The alternative fluid transport device 2700 may be used as the fluid transport device 1770, 1870 in either the microchip 1700 of FIG. 17 or the microchip 1800 of FIG. 18. The fluid transport device 2700 comprises an upper channel 2720A, a lower channel 2720C, and a pump channel 2720B communicating in end-to-end fashion to form a continuous channel 2720. The fluid transport device 2700 includes three arrays 2764, 2765, 2766 of nanochannels having lateral dimensions of nanometer scale, e.g., 1-1000 nm. The channel dimensions can be confined to the nanometer scale in depth or width or both. The channel arrays 2764, 2765, 2766 may consist of one or more nanochannels in a planar or three dimensional configuration.

Two of the nanochannel arrays, first and second bridging arrays 2765, 2766, act as bridging membranes. A first side channel 2725 is provided adjacent the upper channel 2720A and communicates electrically with the pump channel 2720B through the first bridging array 2765. A second side channel 2726 is provided adjacent the lower channel 2720C and communicates electrically with the pump channel 2720B through the second bridging array 2766. The first bridging array 2765 is disposed between the upper channel 2720A and first side channel 2725. Similarly, the second bridging array 2766 is disposed between the lower channel 2720C and second side channel 2726. The bridging arrays 2765, 2766 conduct electric current but inhibit, minimize, or reverse bulk fluid transport therethrough. The third array, pump array 2764, is disposed in the pump channel 2720B. The nanochannels in the pump array 2764 need to support electroosmotic flow and provide sufficient flow resistance to pump against.

In operation, a high voltage is applied near the ends 2710, 2712 of the pump channel 2720B through the bridging arrays 2765, 2766. Indirect application of the electric potential to the pump channel 2720B through the bridging arrays 2765, 2766 prevents gas bubbles from forming in the pump channel 2720B due to electrolysis at the electrodes 2728. No electric field is present in the channel above or below the pump channel 2720B. The arrows in FIG. 27 show the direction of flow.

For this pumping scheme to work, the nanochannels in the pump channel 2720B must have a higher electroosmotic mobility than the nanochannels in the bridging arrays 2765, 2766 to generate the momentum necessary to create a subambient pressure on the pump channel side of the first bridging array 2765 and a superambient pressure on the pump channel side of the second bridging array 2766. For a given buffer concentration, and consequently electrical double layer thickness, the dimensions of the nanochannels in the bridging arrays 2765, 2766 can be fabricated with at least one lateral dimension on the order of the double layer thickness and smaller than the nanochannels in the pump array 2764 such that the average electroosmotic mobility in the bridging arrays 2765, 2766 is lower than the average electroosmotic mobility in the pump array 2764. A larger difference in the electroosmotic mobilities leads to more efficient pumping. Consequently, a difference in the lateral dimensions of the nanochannels is sufficient to induce hydraulic pumping electroosmotically.

In addition to or instead of varying the lateral dimensions of the nanochannels to effect pumping, the surface chemistry of the nanochannels can be modified to electroosmotically induce hydraulic pumping. To support electroosmotic flow in the pump channel 2720B, the nanochannel surfaces should be ionizable and have a reasonable excess charge of either polarity or be electronegative. For example, silicon dioxide is negatively charged in most aqueous buffers and readily supports electroosmotic flow. For the bridging arrays 2765, 2766, nanochannel surfaces that do not exhibit electroosmotic flow or exhibit electroosmotic flow in the opposite direction to the pump channel 2720B are preferable. For example, hydrophilic uncharged polymers bound to channel surfaces inhibit electroosmotic flow, and cationic polyelectrolytes adsorbed to the nanochannel surfaces support electroosmotic flow in the direction opposite that of silicon dioxide. Consequently, the surfaces of the nanochannels in the bridging arrays 2765, 2766 and pump array 2764 can be chemically modified to suppress, reverse, or enhance the electroosmotic flow in order to control pumping efficiency. No electric fields are present in the lower and upper channels 2720C, 2720A during operation of the device.

Methods to fabricate such nanochannels include ion beam milling and electron beam (e-beam) lithography. Focused ion beam milling is effective for fabricating trenches with lateral dimensions down to approximately 10 nm. E-beam lithography coupled with chemical etching can produce channels having similar dimensions. A closed network of channels can then be formed by bonding a cover plate to the substrate.

Figure 22A:
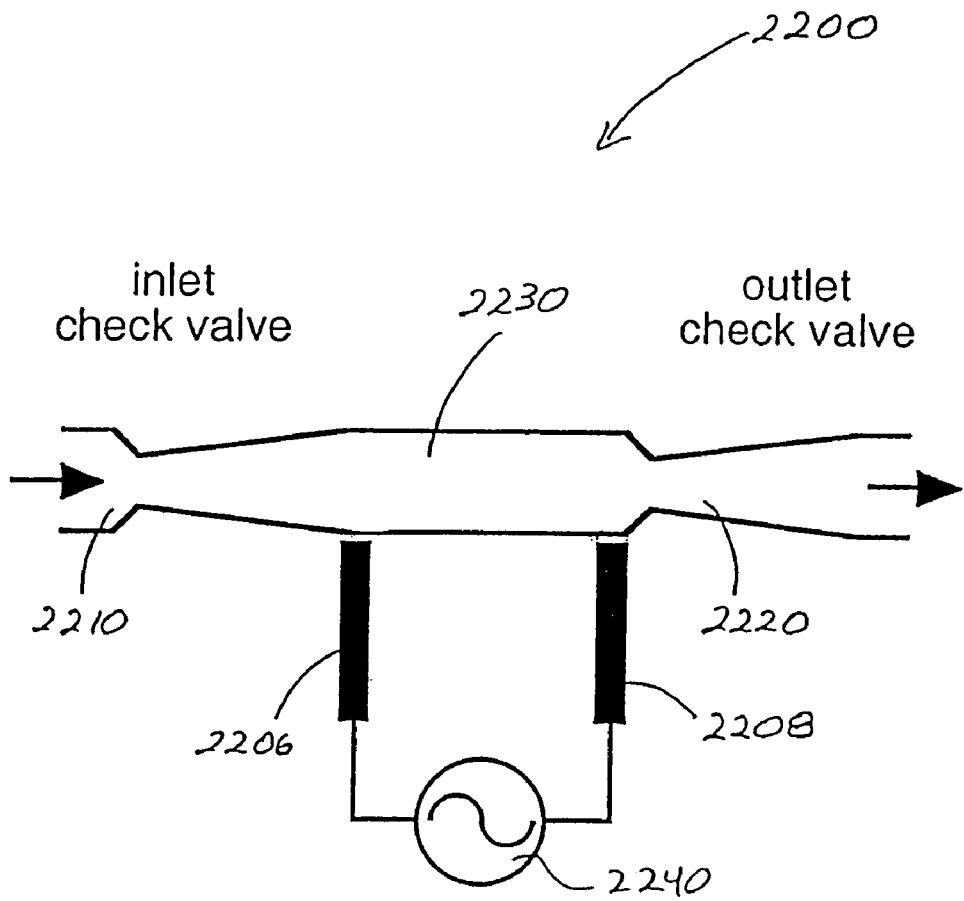
FIGS. 22A and 22B are schematic diagrams of pumping devices comprising two check valves in accordance with a further aspect of this invention.
Figure 22B:
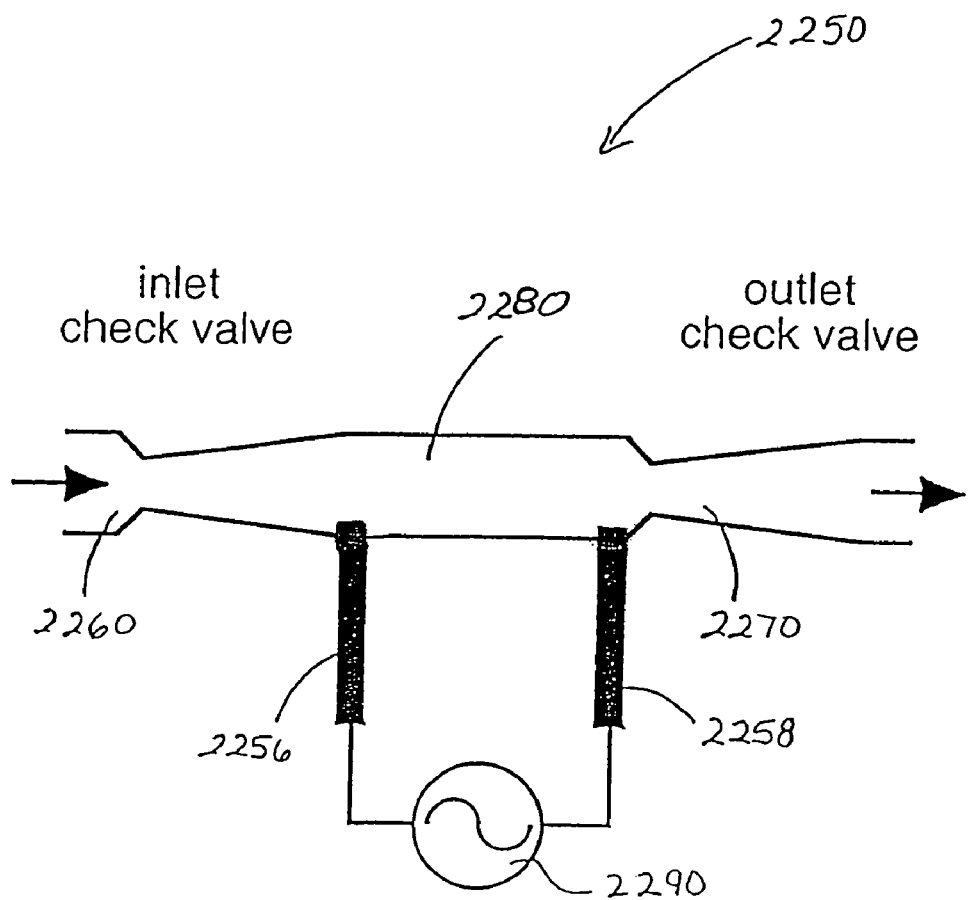

Yet additional embodiments of fluid transport devices in accordance with the present invention, e.g., alternating current (AC) devices, are provided as illustrated in FIGS. 22A and 22B. Check valve fluid transport devices 2200, 2250 may be used as the fluid transport device 1770 in the microchip 1700 of FIG. 17 or the fluid transport device 1870 of the microchip 1800 of FIG. 18. The check valve fluid transport devices 2200, 2250 pump fluids through a channel 2230, 2280 by generating hydraulic pressures electroosmotically. Passive check valves 2210, 2220, 2260, 2270 disposed at either end of the channel 2230, 2280 provide directionality to the flow as described more fully below.

Referring now to FIG. 22A, a first configuration of an AC fluid transport device 2200 is provided having two electrodes 2206, 2208 positioned along and in close proximity to the channel 2230. The electrodes 2206, 2208 can be positioned next to, above, below, or around the channel 2230. An alternating current (AC) electric field is applied between the electrodes 2206, 2208 by a power supply 2240 in electrical contact with the electrodes 2206, 2208. The oscillating electric field moves the fluid in the channel 2230 back and forth electroosmotically, and the inlet and outlet check valves 2210, 2220 allow the fluid to flow preferentially in one direction, as shown by the arrows. The AC electric field is capacitively coupled to the channel 2230 by the electrodes 2206, 2208 and is not in direct electrical contact with the liquid in channel 2230, unlike the membrane configurations of FIGS. 19A, 19B, and 21 which apply DC electric fields through a bridging membrane or unlike configurations where electrodes are in direct contact with the fluid in the channel.

In a second configuration of an AC fluid transport device 2250, as illustrated in FIG. 22B, two electrodes 2256, 2258 are positioned in contact with fluid contained in the channel 2280. An alternating current (AC) electric field is applied between the electrodes 2256, 2258 by a power supply 2290 in electrical contact with the electrodes 2256, 2258. The oscillating electric field moves the fluid in the channel 2280 back and forth electroosmotically, and the inlet and outlet check valves 2260, 2270 allow the fluid to flow preferentially in one direction, as shown by the arrows.

The AC fluid transport devices 2200, 2250 can be fabricated in silicon, glass, or plastic substrates using common fabrication techniques. The fluidic channels 2230, 2280 and passive check valves 2210, 2220, 2260, 2270 can be etched or cast into the substrate. The electrodes 2206, 2208, 2256, 2258 can be fabricated in several ways including depositing thin metal films or etching channels into the substrate and filling these channels with an electrically conductive material, e.g., a low temperature alloy.

The fluid transport devices 2200, 2250 may include one or more check valves, but without at least one check valve the fluid would just oscillate back and forth in the channel 2230, 2280. With two check valves 2210, 2220, 2260, 2270 the pumping efficiency is expected to be higher than with only one check valve. The passive check valves 2210, 2220, 2260, 2270 are relatively easy to fabricate, and the design can be varied depending on the fluid being pumped to achieve the highest efficiency. The fluid transport devices 2200, 2250 are not limited to using passive check valves 2210, 2220, 2260, 2270. Other check valve designs can be integrated into the fluid transport devices 2200, 2250. An AC pumping device of the type shown in FIG. 22 typically pumps fluids that support electroosmotic flow, e.g., buffered aqueous solutions, but may also be able to electrohydrodynamically pump fluids with low conductivities and moderate to high dielectric constants, e.g., organic solvents. Also, two of these pumps can be operated in parallel and out of phase from each other to provide continuous or nearly continuous flow.

Figure 23:
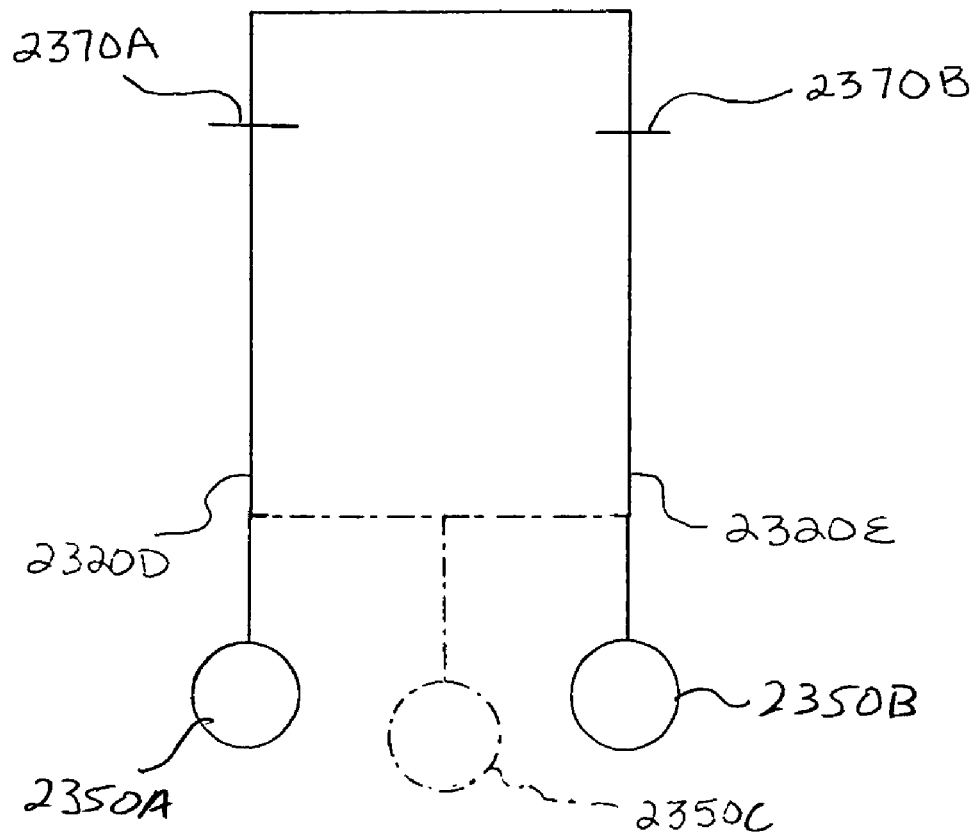
FIG. 23 is a schematic diagram of a further arrangement of microchannels and pumping devices for accomplishing focusing of a stream of fluidic material.

For example, as illustrated in the configurations of FIG. 23, two or more pump channels 2320D, 2320E may be provided in parallel relation to one another, where each pump channel 2320D, 2320E is associated with a respective AC fluid transport device 2370A, 2370B of the type illustrated in FIGS. 22A or 22B. In fluid communication with the output of each check valve fluid transport device 2370A, 2370B, waste reservoirs 2350A, 2350B may be provided. Alternatively, a single waste reservoir 2350C may be provided in fluid communication with the output of each AC fluid transport device 2370A, 2370B as illustrated in phantom in FIG. 23. In such a configuration where only a single waste reservoir 2350C is provided, the waste reservoirs 2370A, 2370B need not be provided.

The AC fluid transport devices 2370A, 2370B are preferably operated out of phase from each other to provide continuous flow through the analysis channel. That is, the phase of the first fluid transport device 2370A may be such that the oscillating fluid motion within the left pump channel segment 2320D is directed towards the associated waste reservoir 2350A while the phase of the second fluid transport device 2370B is such that the oscillating fluid motion within the right pump channel segment 2320E is directed away from the associated waste reservoir 2350B but restricted by the presence of the outlet check valve. Alternatively, the check valve fluid transport devices 2370A, 2370B may be selectively operated so as to deliver a selected segment of fluid to a particular waste reservoir 2350A, 2350B, thus providing a selecting or sorting function.

In addition to providing focusing of a fluid stream in a first transverse direction, additional microchip configurations are provided in accordance with the present invention to promote focusing in a second direction. For example, additional embodiments of channel junctions for use in microchips are illustrated in FIGS. 25A-25C and 26A-26C, where the channel junctions 2530, 2630 are configured to promote focusing of a stream of fluid in the vertical direction, V, in addition to the transverse direction, T. The transverse direction, T, lies in the plane of FIGS. 25A and 26A, along the direction of the axis of the first and second buffer channels 2530A, 2530B, 2630A, 2630B; the vertical direction, V, is oriented perpendicular to the plane of FIGS. 25A and 26A, as illustrated in the side elevational views of FIGS. 25B and 26B.

Figure 25A:
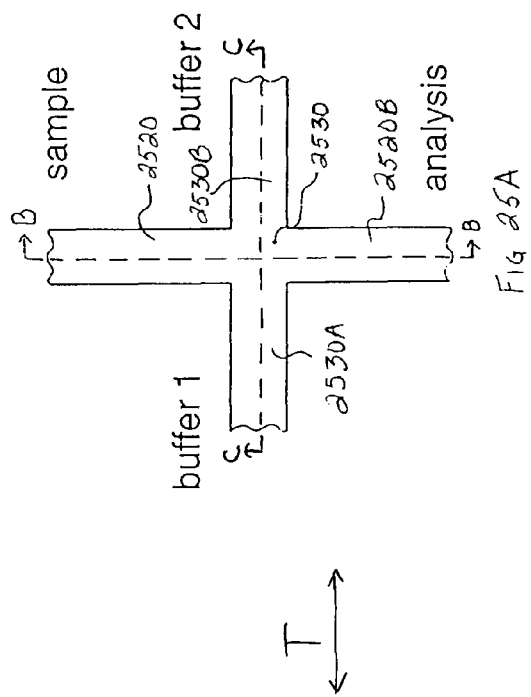
FIGS. 25A-C are schematic diagrams of arrangements of microchannels in accordance with another aspect of this invention for accomplishing two dimensional focusing of a stream of fluidic material.

Referring now to the microchip configuration of FIG. 25A, a top view of a channel junction 2530 of a microchip is illustrated. The channel junction 2530 is similar to the channel junctions 1730, 1830 of microchips 1700, 1800 as illustrated in FIGS. 17 and 18. However, the channel junction 2530 is configured to promote focusing of the sample stream in the vertical direction, V, in addition to the transverse direction, T. In particular, the dimensions of the sample, buffer, and analysis channels 2520, 2530A, 2530B, 2520B are selected to promote focusing in the vertical direction as well as the transverse direction. For example, the sample channel 2520 may have a first selected height, H1, and the buffer and analysis channels 2530A, 2530B, 2520B and the channel junction 2530 have a second selected height, H2, which is greater than the first selected height, H1, FIG. 25B.

Figure 25B:
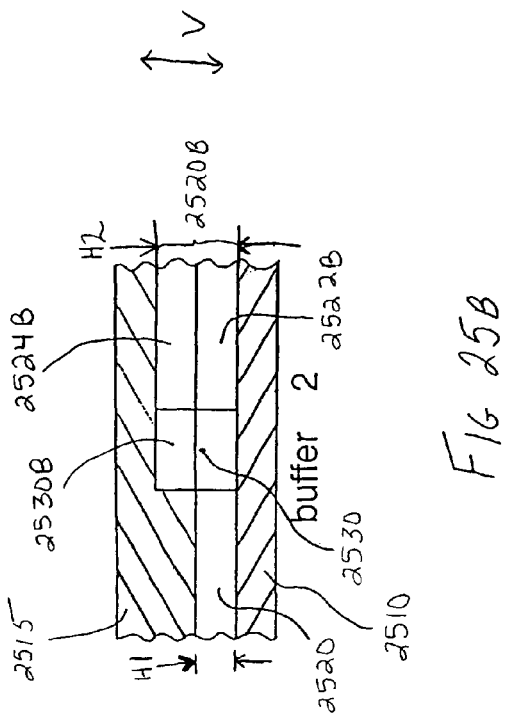
Figure 25C:
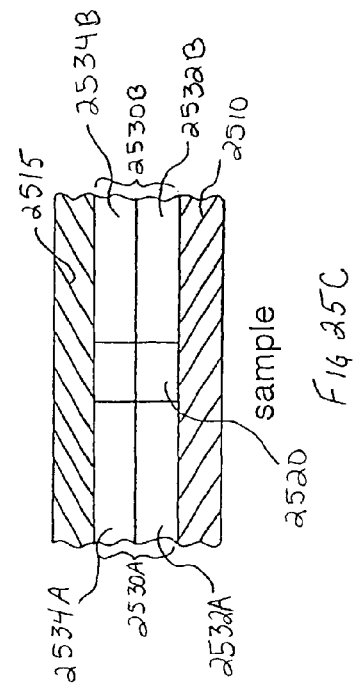

One method for fabricating the channel junction in FIGS. 25A-C is to fabricate a cross intersection in a lower substrate 2510 and a tee intersection in an upper substrate 2515. The cross intersection of the lower substrate 2510 includes sample channel 2520 and buffer 1 channel lower portion 2532A, buffer 2 channel lower portion 2532B, and an analysis channel lower portion 2522B. The tee intersection of the upper substrate 2515 has a buffer 1 channel upper portion 2534A, buffer 2 channel upper portion 2534B, and an analysis channel upper portion 2524B. The two substrates 2510, 2515 are then mated with lower and upper channel portions of the buffer 1, buffer 2, and analysis channel portions registered to one another to form the buffer 1, buffer 2 and analysis channels 2530A, 2530B, 2520B. Since the sample channel 2520 has a height, H1, which is less than the height, H2, of the channel junction 2530, a sample stream is introduced into the vertically lower portion of the channel junction 2530 and is confined in the vertical direction against the bottom of the analysis channel 2520B. In addition, the flow of buffer material through the buffer channels 2530A, 2530B confines a sample stream in the transverse direction in a similar manner as the transverse confinement in the channel junction 1730 of microchip 1700 of FIG. 17. In the case where hydraulic pumping is used, the vertically and transversely confined sample stream has a narrower velocity distribution than an unfocused sample stream or a sample stream focused only in the transverse direction.

Turning now to FIGS. 26A-26C, an alternate configuration of a channel junction 2630 for promoting vertical and transverse focusing of a sample stream to a central region of an analysis channel 2620B is illustrated. The channel junction 2630 is similar to the channel junctions 1730, 1830 of microchips 1700, 1800 as illustrated in FIGS. 17 and 18. However, the channel junction 2630 is configured to promote focusing of the sample stream centrally in the vertical and transverse directions, V, T, respectively. The dimensions of the sample, buffer, and analysis channels 2620, 2630A, 2630B, 2620B are selected to effect the focusing of the sample in the center of the analysis channel 2620B. For example, the sample channel 2620 may have a first selected height, H1, and the buffer and analysis channels 2630A, 2630B, 2620B and the channel junction 2630 may have a second selected height, H2, which is greater than the first selected height, H1, FIG. 26B. Alternatively, the analysis channel 2620B may have the same height as the sample channel 2620.

To form the channel junction 2630 depicted in FIGS. 26A-26C according to a first method, cross intersections may be fabricated in respective upper and lower substrates 2615, 2610. The cross intersection of the lower substrate 2610 includes a sample channel lower portion 2622, a buffer 1 channel lower portion 2632A, buffer 2 channel lower portion 2632B, and an analysis channel lower portion 2622B. The cross intersection of the upper substrate 2615 has a sample channel upper portion 2624, a buffer 1 channel upper portion 2634A, a buffer 2 channel upper portion 2634B, and an analysis channel upper portion 2624B. The two substrates are then mated with lower and upper channel portions of the sample, buffer 1, buffer 2, and analysis channel portions registered to one another to form the sample, buffer 1, buffer 2 and analysis channels 2620, 2630A, 2630B, 2620B. Since the sample channel 2620 has a depth, H1, which is less than the depth, H2, of the channel junction 2630, a sample stream is introduced into the vertically central portion of the channel junction 2630 and is confined in the vertically central portion of the analysis channel 2620B. In addition, the flow of buffer material through the buffer channels 2630A, 2630B confines a sample stream in the transverse direction in a manner similar to the transverse confinement effected in the channel junction 1730 of microchip 1700 (FIG. 17). The channel junction in FIGS. 26A-26C has the added benefit that the confined sample stream does not contact the walls of the analysis channel near the channel junction. Depending on the fabrication methods, the channel walls may not be vertical as depicted in FIGS. 25 and 26.

Several embodiments of a microfabricated device in accordance with the present invention have been described hereinabove. The microfabricated devices which utilize a bridging membrane overcome many of the limitations of the known devices. Devices constructed in accordance with the concepts of this invention permit several advantageous modes of operation. More particularly, an embodiment has been described that provides sample loading and injection with a minimum of electrochemically generated byproducts. Another embodiment of the present invention has been described that enables the transport of fluidic materials by electroosmotic forces in a channel region that is uninfluenced by an electric field. A further embodiment has been described that provides the ability to concentrate ionic species in an analysis channel. Still other embodiments of the present invention have been described which facilitate the separation or purification of sample material, that facilitate the removal of electrochemically generated gas species from the sample and transport materials, that provide either positive or negative pressure to facilitate hydraulic transport of fluidic materials, and that provide valving of fluidic materials in a microfluidic structure. Still further embodiments are described which provide novel means for confining or focusing a stream of fluidic material and means for pumping such material that utilizes one or more bridging membranes.

The terms and expressions which have been employed are used as terms of description and not of limitation. There is no intention in the use of such terms and expressions of excluding any equivalents of the features shown and described or portions thereof. For example, other pressure source and electrokinetic transport can be used in one or more of the devices and methods described above to effect focusing, e.g., the devices of FIGS. 25 and 26. It is recognized, however, that various modifications such as channel dimension, location, and arrangement are possible within the scope of the invention as claimed.

What is claimed is:

1. A check valve microfluidic transport device comprising:
   a microfluidic pump channel formed in a substrate for conducting a stream of fluid therethrough;
   a first check valve formed in the substrate having an inlet end and an outlet end, the inlet and outlet ends being disposed in spaced-apart relation, said check valve being in fluid communication with a first end of said microfluidic pump channel;
   an AC power supply; and
   a plurality of electrodes disposed proximate to said microfluidic pump channel, the plurality of electrodes electrically coupled to the AC power supply to provide an oscillating electric field to a fluid within said microfluidic pump channel, whereby cooperation between the check valve and oscillating electric field imparts a preferential flow direction to the stream of fluid by generating hydraulic pressures electroosmotically.

2. A check valve microfluidic transport device as set forth in claim 1, wherein one or more of the electrodes is positioned externally to the interior of said microfluidic pump channel and said electrode is adapted to capacitively couple an electric field to the fluid disposed within said microfluidic pump channel.

3. A check valve microfluidic transport device as set forth in claim 1, wherein one or more of the electrodes extends into the interior of said microfluidic pump channel, said electrode adapted to electrically contact the fluid disposed in the interior of said microfluidic pump channel.

4. A check valve microfluidic transport device as set forth in anyone of claims 1, 2, or 3, wherein said fluid transport device comprises a second check valve formed in the substrate, said second check valve being in fluid communication with a second end of said microfluidic pump channel.

5. A check valve microfluidic transport device as set forth in any one of claim 1, 2, or 3, comprising:
   a second microfluidic pump channel formed in the substrate for conducting a stream of fluid therethrough, the second microfluidic pump channel disposed in fluid communication with the first microfluidic pump channel;

a second check valve formed in the substrate having an inlet end and an outlet end, the inlet and outlet ends being disposed in spaced-apart relation, the second check valve being in fluid communication with a first end of the second microfluidic pump channel;

a second AC power supply; and a second plurality of electrodes disposed proximate to the second microfluidic pump channel, the second plurality of electrodes electrically coupled to the AC power supply to provide an oscillating electric field to a fluid within the second microfluidic pump channel, whereby cooperation between the second check valve and oscillating electric field imparts a preferential flow direction to the stream of fluid in the second microfluidic pump channel by generating hydraulic pressures electroosmotically.

6. The check valve microfluidic transport device of claim 5, wherein the power supplies are operated out of phase from one another to provide continuous flow through an analysis microchannel.

* * * * *